(12) United States Patent
Thompson

(10) Patent No.: US 6,711,437 B2
(45) Date of Patent: Mar. 23, 2004

(54) PACING CHANNEL ISOLATION IN MULTI-SITE CARDIAC PACING SYSTEMS

(75) Inventor: David L. Thompson, Andover, MN (US)

(73) Assignee: Medtronic, Inc., Minneapolis, MN (US)

(*) Notice: Subject to any disclaimer, the term of this patent is extended or adjusted under 35 U.S.C. 154(b) by 235 days.

(21) Appl. No.: 09/918,225

(22) Filed: Jul. 30, 2001

(65) Prior Publication Data

US 2003/0023280 A1 Jan. 30, 2003

(51) Int. Cl.[7] .............................................. A61N 1/08
(52) U.S. Cl. .................................................... 607/9
(58) Field of Search .............................. 607/4, 5, 9, 27, 607/30

(56) References Cited

U.S. PATENT DOCUMENTS

| | | |
|---|---|---|
| 3,757,791 A | 9/1973 | Berkovits |
| 3,766,413 A | 10/1973 | Berkovits |
| 3,814,106 A | 6/1974 | Berkovits |
| 3,835,865 A | 9/1974 | Bowers |
| 4,170,999 A | 10/1979 | Allen et al. |
| 4,275,737 A | 6/1981 | Thompson et al. |
| 4,310,000 A | 1/1982 | Lindemans |
| 4,379,459 A | 4/1983 | Stein |
| 4,406,286 A | 9/1983 | Stein |
| 4,476,868 A | 10/1984 | Thompson |
| 4,498,478 A | 2/1985 | Bourgeois |
| 4,649,931 A | 3/1987 | Beck |
| 4,726,380 A | 2/1988 | Vollmann et al. |
| 4,800,883 A | 1/1989 | Winstrom |
| 4,811,738 A | 3/1989 | Economides et al. |
| 4,830,006 A | 5/1989 | Haluska et al. |
| 4,850,357 A | 7/1989 | Bach, Jr. |
| 4,880,005 A | 11/1989 | Pless et al. |
| 4,953,551 A | 9/1990 | Mehra et al. |
| 4,998,531 A | 3/1991 | Bocchi et al. |

(List continued on next page.)

FOREIGN PATENT DOCUMENTS

| | | | |
|---|---|---|---|
| EP | 9218198 | 10/1992 | |
| WO | WO 99/55415 | 11/1999 | .......... A61N/1/368 |

OTHER PUBLICATIONS

W.L. Hui et al., "Monolithic 4–20mA Isolating Current Replicator Using GMR Resistors", Session 17, Sensor Technology, Paper SA 17.5, Feb. 7, 1998, p. 280–281.*

(List continued on next page.)

Primary Examiner—Jeffrey R. Jastrzab
Assistant Examiner—Frances P. Oropeza
(74) Attorney, Agent, or Firm—Girma Wolde-Michael; Paul H. McDowall

(57) ABSTRACT

Cardiac pacing systems are disclosed for providing multi-site pacing in a single heart chamber or multi-chamber pacing in two or more heart chambers employing N pacing channels and miniaturized electrical isolation circuitry in up to N–1 pacing channels to minimize the effects of leakage currents generated during delivery of a pacing pulse in any one pacing channel from affecting sense amplifiers in the other pacing channels. Isolation of a the pace/sense electrodes from leakage currents is effected employing monolithic isolation circuit means. An isolated current replicator employing giant magnetoresistive (GMR) sense elements in conjunction with isolated planar cells fabricated in monolithic form is incorporated into conventional VLSI circuitry. Or, the monolithic isolation circuit means is formed of a micro-mechanical fabricated (MEMS) isolation transformer comprising low-loss input and output coils separated by an insulation layer that isolates the input coil from the output coil.

12 Claims, 8 Drawing Sheets

U.S. PATENT DOCUMENTS

| | | | |
|---|---|---|---|
| 5,117,824 | A | 6/1992 | Keimel et al. |
| 5,156,149 | A | 10/1992 | Hudrlik |
| 5,163,427 | A | 11/1992 | Keimel |
| 5,178,140 | A | 1/1993 | Ibrahim |
| 5,265,588 | A | 11/1993 | Nelson et al. |
| 5,292,338 | A | 3/1994 | Bardy |
| 5,722,998 | A | 3/1998 | Prutchi et al. |
| 5,836,981 | A | 11/1998 | Chang et al. |
| 5,902,324 | A * | 5/1999 | Thompson et al. ............ 607/9 |
| 5,929,636 | A | 7/1999 | Torok et al. |
| 6,031,273 | A | 2/2000 | Torok et al. |
| 6,054,780 | A | 4/2000 | Haigh et al. |
| 6,087,882 | A | 7/2000 | Chen et al. |
| 6,101,417 | A | 8/2000 | Vogel et al. |
| 6,252,390 | B1 | 6/2001 | Black, Jr. et al. |

OTHER PUBLICATIONS

Olson et al., "Onset and Stability for Ventricular Tachyarrhythmia Detection in an Implantable Pacer–Cardioverter–Defibrillator", IEEE Computer Society Press, Oct. 7–10, 1986 p. 167–170.

Arzbaecher, "Automatic Tachycardia Recognition" PACE, May–Jun. 1984, p. 541–547.

W.L. Hui et al., "Monolithic 4–20mA Isolating Current Replicator Using GMR Resistors", Session 17, Sensor Technology, paper SA 17.5, Feb. 7, 1998, p. 280–281.

T.M. Hermann et al., "Magnetically Coupled Linear Isolator", IEEE Transactions on Magnetics, vol. 33, No. 5, p. 4029–4031, Sep. 1997.

Marwan M. Hassoun et al., "Field Programmable Logic Gates Using GMR Devices", IEEE Transactions on Magnetics, vol. 33, No. 5, p. 3307–3309, Sep. 1997.

Magnetoresistive Isolators Advance the Drive Toward Component Miniaturization, Sensors, Jan. 1999, p. 59–60.

* cited by examiner

PACING CHANNEL ISOLATION IN MULTI-SITE CARDIAC PACING SYSTEMS

CROSS-REFERENCE TO RELATED APPLICATIONS

Reference is hereby made to commonly assigned U.S. patent application Ser. No. 09/867,097 filed on May 29, 2001 for HIGH VOLTAGE SWITCH ISOLATION FOR IMPLANTABLE CARDIOVERTERS/DEFIBRILLATORS filed in the name of David L. Thompson.

FIELD OF THE INVENTION

The present invention pertains to cardiac pacing systems for providing multi-site pacing in a single heart chamber or multi-chamber pacing including AV sequential pacing and sensing in at least one upper and one lower heart chamber and/or bi-atrial pacing or bi-ventricular pacing involving pacing and sensing in two, three, or four heart chambers and particularly to employing miniaturized electrical isolation circuitry at the inputs of least one of the sense amplifiers associated with a site or heart chamber to improve the sensing of cardiac depolarizations following delivery of a pacing pulse at another site or heart chamber.

BACKGROUND OF THE INVENTION

The cardiovascular system provides oxygenated blood to various structures of the body. In a normally functioning heart, the body's demand for oxygenated blood varies, and the heart responds by increasing or decreasing its rate and force of contraction to meet the demand. An electrical signal generated by the sinus node in the upper right atrial wall near the base of the heart is conducted through the upper heart chambers, i.e., the right and left atria, and causes them to contract in a synchronous manner. The contraction of the upper heart chambers forces blood pooled therein through open heart valves and into the right and left ventricles or lower heart chambers. The atrial electrical depolarization wave arrives at the AV node superior to the ventricles and triggers the conduction of a ventricular depolarization wave down the bundle of His in the septum between the right and left ventricles to the apex of the heart. The ventricles contract after a brief atrio-ventricular (AV) delay time following the sinus node depolarization as the depolarization wave then advances superiorly, posteriorly, and anteriorly throughout the outer ventricular wall of the heart. The lower heart chambers contract and force the blood through the vascular system of the body. The contraction of the right and left ventricles proceeds in an organized fashion which optimizes emptying of the ventricular chambers. The synchronous electrical depolarization of the atrial and ventricular chambers can be electrically sensed and displayed, and the electrical waveform is characterized by accepted convention as the "PQRST" complex. The PQRST complex includes the P-wave, corresponding to the atrial depolarization wave, the R-wave, corresponding to the ventricular depolarization wave, and the T-wave which represents the re-polarization of the cardiac cells.

Various disease mechanisms cause conduction disturbances which interfere with the natural conduction system of the heart and affect the heart's ability to provide adequate cardiac output to the body. In certain disease mechanisms, the sinus node fails to depolarize and commence the P-wave as rapidly as required to satisfy the demand for oxygenated blood, or the atria may spontaneously depolarize at rates that are well in excess of the ability of the ventricles to respond. In these situations, the ventricles may compensate by depolarizing spontaneously from ectopic depolarization sites. In other cases where the SA node operates correctly, 1:1 atrial and ventricular depolarization synchrony is lost because the AV node fails to respond to all P-waves or a defect in the bundle of His interferes with the conduction of the ventricular depolarization. In all of these cases, the ventricles may contract at an inadequate rate to provide adequate cardiac output.

When the atria or ventricles contract too slowly, the patient may be a candidate for implantation with a cardiac pacemaker for restoring the heart rate by applying pacing pulses to the heart chamber that is malfunctioning at a pacing rate that restores adequate cardiac output. Modern implantable cardiac pacemakers comprise an implantable pulse generator (IPG) and a lead or leads extending from the IPG to pace/sense electrode or electrodes located with respect to the heart chamber to deliver the pacing pulses and sense the P-wave or R-wave. Typically, the leads are transvenously introduced into the particular heart chamber via the superior vena cava and right atrium, and the pace/sense electrodes are maintained in contact with the pace/sense electrode or electrodes located with respect to the heart chamber to deliver the pacing pulses and sense the P-wave or R-wave. Typically, the leads are transvenously introduced into the particular heart chamber via the superior vena cava and right atrium, and the pace/sense electrodes are maintained in contact with the heart tissue by a fixation mechanism at the distal end of the lead. However, leads may be placed subcutaneously between the IPG and the exterior of the heart, and the pace/sense electrodes attached to the epicardium at the desired sites. Moreover, endocardial coronary sinus leads are introduced through the right atrium into the coronary sinus and the great vein to locate pace/sense electrodes in proximity to the left atrium or the left ventricle.

A single chamber, demand pacemaker is implanted to supply pacing pulses to a single upper or lower heart chamber, typically the right atrium or right ventricle, in response to bradycardia of the same chamber. In an atrial, demand pacemaker operating in the AAI pacing mode, an atrial pacing pulse is delivered to the atrial pace/sense electrodes by the IPG if a P-wave is not sensed by an atrial sense amplifier coupled to the atrial pace/sense electrodes within an atrial escape interval (A—A interval) timed by an atrial escape interval timer. In a ventricular, demand pacemaker operating in the VVI pacing mode, a ventricular pacing pulse to the ventricular pace/sense electrodes if an R-wave is not sensed by a ventricular sense amplifier coupled to the ventricular pace/sense electrodes within a ventricular escape interval (V—V interval) timed by a ventricular escape interval timer.

A dual chamber, demand pacemaker is implanted to supply pacing pulses when required to one upper heart chamber and to one lower heart chamber, typically the right atrium and right ventricle. In a dual chamber, demand pacemaker operating in the DDD pacing mode, both the AAI and VVI pacing modes are followed under the above defined conditions. A ventricular pacing pulse is delivered to the ventricular pace/sense electrodes if an R-wave is not sensed by the ventricular sense amplifier coupled thereto within an AV time interval timed from the sensing of a P-wave by the atrial sense amplifier.

Over the years, it has been proposed that various conduction disturbances involving both bradycardia and tachycardia of a heart chamber could benefit from stimulation applied at multiple electrode sites positioned in or about it in synchrony with a depolarization which has been sensed at least one of the electrode sites. In addition, it has been proposed to employ pacing to compensate for conduction defects and in congestive heart failure where depolarizations that naturally occur in one upper or lower chamber are not conducted quickly enough to the other upper or lower heart chamber. In such cases, the right and left heart chambers do not contract in optimum synchrony with each other, and cardiac output suffers due to the timing imbalance. In other cases, spontaneous depolarizations of the left atrium or left ventricle occur at ectopic foci in these left heart chambers, and the natural activation sequence is grossly disturbed. In such cases, cardiac output deteriorates because the contractions of the right and left heart chambers are not synchronized sufficiently to eject blood therefrom.

In patients suffering from congestive heart failure, the hearts become dilated, and the conduction and depolarization sequences of the heart chambers may exhibit Intra-Atrial Conduction Defects (IACD), Left Bundle Branch Block (LBBB), Right Bundle Branch Block (RBBB), and Intra Ventricular Conduction Defects (IVCD). Single and dual chamber pacing of the right atrium and/or right ventricle can be counterproductive in such cases, depending on the defective conduction pathway and the locations of the pace/sense electrodes.

A number of proposals have been advanced for providing pacing therapies to alleviate these conditions and restore synchronous depolarization of right and left, upper and lower, heart chambers as described in commonly assigned U.S. Pat. No. 5,902,324 and references disclosed therein. Typically, the right atrium is paced at expiration of an A—A escape interval, and the left atrium is simultaneously paced or synchronously paced after a short delay time. Similarly, the right ventricle is paced at expiration of a V—V escape interval, and the left ventricle is simultaneously paced or synchronously paced after a short delay time. Some of these patents propose limited forms of DDD pacing having "bi-ventricular" or "bi-atrial" demand or triggered pacing functions. A pacing pulse delivered at the end of an escape interval or at the end of an AV delay (a "paced event") triggers the simultaneous or slightly delayed delivery of the pacing pulse to the other heart chamber.

The above-referenced '324 patent proposes pacing a right heart chamber (RHC) or left heart chamber (LHC) at the end of the escape interval or an AV delay. Pacing in the other of the RHC or LHC is inhibited if a conducted depolarization is detected in that other heart chamber within a physiologic time related to the location of the pace/sense electrodes and referred to therein as a conduction delay window (CDW).

These approaches show promise in restoring the synchronous contractions of the right and left heart chambers in diseased hearts having significant conduction disturbances of the right and left heart depolarization waves but fail to preserve right and left heart synchrony in a physiologic manner. Significant conduction disturbances between the right and left atria can result in left atrial flutter or fibrillation that can be suppressed by pacing the left atrium synchronously with right atrial pacing or sensing of P-waves. And, particularly in patients suffering from heart failure, left atrial and left ventricular cardiac output can be significantly improved when left and right chamber synchrony is restored.

All of the above-described pacing systems operate in demand and/or triggered and/or synchronous modes that depend upon the ability to accurately sense P-waves and/or R-waves at one or more site or heart chamber in the presence of electromagnetic interference (EMI) and in as short a time as possible following delivery of a pacing pulse. A "pacing channel" is defined for each pacing site of a single chamber, multi-chamber or multi-site pacing system, by the lead, the pacing output circuit, the sense amplifier, and associated circuitry coupled to the lead extending to the pace/sense electrode pair for that site. The inputs of the sense amplifier and an output capacitor of the output circuit are commonly coupled to the respective pace/sense electrode pair. Pacing pulses are delivered to the pair of pace/sense electrodes of the pacing channel wherein at least one of the pace/sense electrodes is at pacing site and the other, indifferent, pace/sense electrode is either located on the lead close thereto to provide bipolar pacing and sensing or located at a more remote location, e.g., the case or can of the IPG, to provide unipolar pacing and sensing. In either case, the indifferent pace/sense electrodes of all of the pacing channels are all typically electrically connected in common and with a common ground circuit of the pacing circuitry. The battery is also typically connected to the common ground circuit. Low resistance coupling components of the pacing output circuits can also conduct leakage currents to the active pace/sense electrodes of the pace/sense electrode pairs of two or more pacing channels.

For a number of reasons, it is often difficult to sense P-waves, R-waves or other signals of the PQRST complex caused by a paced depolarization or a spontaneous depolarization for a time following delivery of a pacing pulse in the same channel or in another channel. The lead conductors, the "electrode-tissue interface" of the pace/sense electrode pair with cardiac tissue or fluid, and the mass of cardiac tissue or fluid between the pace/sense electrode pair comprise a capacitive-resistive reactance presented to the output of the output circuit and the input of the sense amplifier of the pacing channel. Pacing pulses are typically delivered by partial discharge of a charged output capacitor into the capacitive-resistive reactance of the pacing channel coupled directly therewith, and the output capacitor recharges during the interval between pacing pulses. The pacing pulse energy is directly delivered to the "same channel", pace/sense electrode pair as intended, but leakage current or "cross-talk" can be conducted "cross-channel" through the pacing system common ground and coupling components to the pace-sense electrode pairs or the non-paced pacing channels.

The discharge of an output capacitor results in same-channel or cross-channel after-effects due to the disruption of the electrical equilibrium condition at the tissue-electrode interface by the discharge current or leakage current, respectively, resulting in polarization of the tissue's intrinsic dipole moments. These stimulation caused "after-potentials" manifest themselves to traditional pacemaker sense amplifiers coupled to a pace/sense electrode pair as decaying voltage signals that persist for a period of time following delivery of pacing pulses until the electrical equilibrium condition is restored. These after-effects interfere with the sense amplifier's ability to sense depolarizations of the heart closely following or caused by delivery of stimulation pulses.

Various attempts have been made in the prior art to counteract the after-potentials of the pacing pulse and simultaneously recharge the output capacitor by means of a "fast recharge" current delivered through the pace/sense electrode pair following the trailing edge of the pacing pulse, as exemplified by U.S. Pat. Nos. 4,476,868, 4,406,286, 3,835,865 and 4,170,999. However, simply passing sufficient current through the electrode-tissue interface to recharge the output capacitor does not necessarily return the electrode-tissue system to its prior electrical equilibrium condition. Alternatively, it has been suggested to counteract the after-effects of delivery of a stimulation pulse by simply tying the electrodes involved in delivery of the pulse together following delivery of the pulse, as disclosed in U.S. Pat. No. 4,498,478 or by means of a train of low energy pulses as disclosed in U.S. Pat. No. 4,811,738.

As set forth in the '324 patent and in commonly assigned U.S. Pat. No. 5,156,149, very high impedance P-wave and R-wave sense amplifiers that do not substantially load the signal source have been employed in pacing systems since the time that integrated circuit (IC) technology was adopted. The sense amplifier has undergone steady development and refinement as reflected by the teachings of commonly assigned U.S. Pat. Nos. 4,275,737, 4,379,459, and 4,649,931. However, the underlying design philosophy, requiring high impedance and high gain in order to sense the low level signal generated by the heart, has remained the same over the years. Band pass filters, time domain filtering, and amplitude threshold comparison continue to be employed to discriminate a P-wave or R-wave from EMI and same channel and cross-channel after-potentials persisting from a prior pacing pulse applied to the same channel or cross-channel pace/sense electrode pair. The prior art, high input impedance, sense amplifier circuits are easily saturated by the pacing pulse delivered between the pace/sense electrodes coupled to the input terminals of the sense amplifier or delivered between other chamber or other site pace/sense electrodes.

When the first AV-sequential, DVI dual chamber pacing systems were developed as shown in U.S. Pat. Nos. 3,757,791, 3,766,413, and 3,814,106, it was found convenient to electrically isolate the atrial sense electrodes from the ventricular pace/sense electrodes through an isolation transformer. However, this approach employing relatively bulky wire wound transformers was abandoned with adoption of IC fabrication technology enabling the miniaturization of the IPG circuitry and the inability of obtaining sufficiently small and reliable discrete component transformers.

It has also been suggested to minimize interaction between the sensing and pacing functions by dedicating separate lead conductors and electrodes to the pacing pulse output circuit and the sense amplifier input terminals as described for example in commonly assigned U.S. Pat. No. 4,310,000. However, lead size and limited IPG can feedthrough space and connector size considerations have to this time dictated use of IPG connector and lead systems having pace/sense electrodes that are shared as described above.

Presently, the sense amplifier input terminals are typically un-coupled from the pace/sense electrodes for a predetermined "blanking" period started on delivery of a pacing pulse across the same channel pace/sense electrode pair or on delivery of a pacing pulse to the pace/sense electrode pair of any other pacing channel to help prevent saturation due to the pacing pulse energy. The blanking period typically extends for a further time period to allow the after-potentials at the electrode-tissue interface to dissipate sufficiently to reliably sense the cardiac signal of interest. The blanking switches typically comprise a single FET switch that is connected in series with one or both of the sense amplifier inputs that are normally closed but are opened during the blanking period and/or another FET switch that is coupled across the input terminals that is normally open but is closed during the blanking period. Exemplary blanking circuitry is disclosed in commonly assigned U.S. Pat. No. 4,401,119, for example. The typical same channel blanking period is about 100 msec in duration and the typical cross-channel blanking period is about 30 msec in contemporary pacemaker IPGs.

Before the adoption of IC fabrication, sense amplifiers were formed of rather bulky discrete components assembled as hybrid circuitry. Blanking was effected in single chamber pacing systems by preventing the sense amplifier output signal from being used by downstream pacemaker circuitry. Sense amplifiers and pacing output circuitry have been fabricated employing discrete components and bipolar ICs mounted in a hybrid package. Timing and control functions have been implemented employing digital IC fabrication techniques, in recent years incorporating a microprocessor, memory and associated components forming a microcomputer and mounted on a substrate. Most recently, linear and sub-micron CMOS fabrication techniques have been adopted that consolidate all of the pacing IPG circuitry except for certain discrete components on a single chip. This has made it more difficult to shorten blanking periods because of reduced voltage breakdown and circuit cross-talk.

In the context of bi-atrial or bi-ventricular sensing and pacing systems described above in reference to the '324 patent, it would be desirable to program the CDW for sensing a conducted depolarization in one heart chamber responding to a pace pulse or sensed event in the other chamber between 5–10 msec and 100 msec, for example. The CDW time depends on the physical locations of the right and left chamber pace/sense electrodes and normal conduction time delays therebetween. In this range, the after-potentials from a pace pulse delivered in the other chamber and reflected to the pace/sense electrodes in the chamber being timed will obscure any underlying evidence of a conducted cardiac depolarization occurring within the CDW time. Use of the typical 100 msec blanking period to overcome the after-potentials problem would prevent the sense amplifier from sensing the conducted depolarization wave.

In the '324 patent, it is suggested that a "field density clamp" circuit be employed that treats the pace/sense electrode pair as two electrode poles and loads the two electrode poles to measure the amount of current injected into the lead system by a passing wavefront. It is asserted that the field density clamp detection system is especially suited to systems in which pacing and sensing functions share electrode poles since this detection strategy is relatively insensitive to the so called "electrode polarization" effects caused by the delivery of pacing energy to excitable tissue, through a lead system. In operation, the active circuitry establishes and maintains the electric field density required to maintain an equilibrium condition between the two poles. The field perturbation caused by the passing wavefront is nulled out by the active circuitry which attempts to balance the potentials at the electrodes. The amount of current supplied to the electrode surfaces through a virtual load, that is required to maintain this null condition, is monitored and forms the basis for the detection of the passing depolarization wavefront. It is preferred to also monitor the voltage across the virtual load and multiply it with the current measurement to characterize the power delivered to the electrode system by the passing depolarization wavefront. Unfortunately, this sensing concept inherently involves an unacceptable current drain at high sensing rates, e.g., during tachyarrhythmia episodes, as compared to conventional sense amplifiers and is susceptible to EMI from several sources.

In all of the above-described examples and in others that will occur to those of skill in the art, it remains desirable to reduce the blanking periods of sense amplifiers employed to sense a conducted or natural cardiac depolarization across a pair of pace/sense electrodes after delivery of a pacing pulse to the same or a different pair of pace/sense electrodes. The reduction in the blanking periods must be effected in a manner that does not increase the size of the pacing system or increase current consumption from the IPG battery.

SUMMARY OF THE INVENTION

The present invention is therefore directed to reducing the blanking periods of sense amplifiers employed to sense a cardiac depolarization across a pair of pace/sense electrodes after delivery of a pacing pulse to the same or a different pair of pace/sense electrodes in at least a two site or chamber pacing system. The present invention incorporates monolithic isolation circuit means comprising an output current loop coupled with a pair of pace/sense electrodes and an input current loop coupled to the sense amplifier inputs, the input and output current loops formed as integrated circuit conductors and functioning as isolated current replicators of sensed cardiac depolarizations. In a multi-site or multi-chamber pacing system having N sense amplifiers in N sense amplifier channels, N−1 isolated current replicators are in circuit between the pace/sense electrodes and the sense amplifier inputs of up to N−1 sense amplifiers.

Preferably, each isolated current replicator is also in circuit between the pacing pulse generator and the pair of pace/sense electrodes of the channel. The output current loop is coupled with the pair of pace/sense electrodes of the channel, and the input current loop is coupled with both the input of the sense amplifier and the output of the pacing pulse generator. In this embodiment, pacing trigger pulses delivered to the input current loop are replicated in the output current loop and delivered to the pace/sense electrodes, whereas cardiac signals traversing the pace/sense electrodes and the output current loop are replicated in the input current loop and provided to the sense amplifier.

The input current loop and the output current loop are isolated from one another so that the output current loop and the components coupled therewith, including the pace/sense electrode pair of the pacing channel are uncoupled from the pacing circuitry and isolated from leakage currents accompanying delivery of a pacing pulse to a pace/sense electrode pair of another pacing channel. The output current loop is isolated from the pacing circuitry coupled to the input current loop to prevent cross-channel leakage current accompanying delivery of a pacing pulse in another pacing channel from being applied to the pace/sense electrode pair coupled with the output current loop. Thus, after-potentials do not develop on the isolated pace/sense electrode pair, and the blanking period can be substantially reduced.

Preferably, a first blanking period is commenced for each sense amplifier coupled with a current replicator input current loop when a pacing pulse is delivered to the same channel pace/sense electrode pair that is connected to the input current loop. A second blanking period is commenced when the cross-channel pacing pulse is applied to a different pace/sense electrode pair than is connected to the input current loop. In the latter case, the blanking period can be set to zero or the width of the pacing pulse and associated recharge time or about 5 msec to about 10 msec. In the former case, the blanking period can be set to a range of about 50 msec to about 100 msec.

In one embodiment, the isolated current replicator is formed employing giant magnetoresistive (GMR) elements, each GMR element comprising a GMR inductor associated with a GMR resistor fabricated in monolithic form isolated planar cells and incorporated into conventional VLSI circuitry. The input and output current loops are formed with GMR inductors associated with GMR resistors that are in turn coupled in a bridge circuit with the inputs of an operational amplifier. The output current loop is coupled to the output of the operational amplifier and with the pair of pace/sense electrodes of the pacing channel. The input current loop is coupled to the inputs of the sense amplifier and the output of a pacing pulse generator of the pacing channel.

In a further embodiment, the isolated current replicator is formed of a micro-mechanical fabricated (MEMS) isolation transformer comprising low-loss input and output coils separated by an insulation layer that isolates the input coil from the output coil.

The present invention can be implemented in various multi-site and multi-chamber pacing systems, preferably in multi-chamber pacing systems providing pacing and sensing in an upper and lower heart chamber or in two upper heart chambers or in two lower heart chambers or in three or four heart chambers that provide synchronous pacing of upper and lower and/or right and left heart chambers as needed. Such pacing systems of the present invention overcome the problems and limitations of the multiple chamber pacing systems described above and provide a great deal of flexibility in tailoring the delivered pacing therapy to needs of the individual patient's heart.

The isolated current replicator can be advantageously employed with conventional capacitive discharge pacing output circuits and sense amplifiers.

In addition, the use of the Isolated current replicator coupled with the pace/sense electrodes allows the morphology of spontaneous and evoked depolarizations conducted from a spontaneous or evoked depolarization in the other chamber to be analyzed to determine pathologies of the conduction pathways.

The present invention offers numerous advantages in providing right and left heart pacing to patient's suffering from advanced congestive heart failure and exhibiting IACD, LBBB, RBBB, and/or IVCD. In the particular case where a CDW is timed out, the ability to sense a conducted evoked or spontaneous depolarization in one of the right or left heart chambers within a very short CDW from the pacing pulse or spontaneous depolarization to the other heart chamber is enhanced by use of the isolated current replicator. Longevity is enhanced by the inhibition of the delivery of pacing pulses by sensed events detected within the respective controlling CDW. The various operating modes of the IPG and each CDW and each AV delay can be programmed during chronic implantation to adjust to observed changes in the underlying electrical activation sequence as the patient's condition improves or deteriorates.

BRIEF DESCRIPTION OF THE DRAWINGS

These and other objects, advantages and features of the present invention will be more readily understood from the following detailed description of the preferred embodiments thereof, when considered in conjunction with the drawings, in which like reference numerals indicate identical structures throughout the several views, and wherein.

DETAILED DESCRIPTION OF THE PREFERRED EMBODIMENTS

In the following detailed description, references are made to illustrative embodiments for carrying out the invention wherein an isolated current replicator circuit is located between the pace/sense electrodes and the sense amplifier inputs of up to N−1 sense amplifiers of a pacing system comprising N sense amplifiers It is understood that other embodiments may be utilized without departing from the scope of the invention. For example, a first preferred embodiment of the invention is disclosed hereafter utilized in the context of a bi-chamber pacing system or pacemaker operating in demand and triggered pacing modes for restoring synchrony in depolarizations and contraction of left and right heart chambers for treating bradycardia in those chambers. A second preferred embodiment of the invention is also disclosed in the context of a four chamber pacing system or pacemaker having an AV sequential operating mode for restoring right and left heart chamber depolarization synchrony of the upper and lower heart chambers. The four chamber pacing system is configurable to function as a three chamber pacing system by selectively disabling one of the upper or lower pacing chambers. It will also be appreciated that the two chamber, three chamber or four chamber pacing systems and methods described herein in detail can be implanted and employed in treatment of an electrical conduction disturbance in a single heart chamber or between two heart chambers.

It will also be understood that the present invention can be implemented in the context of a dual chamber pacing system or pacemaker operating in a DDD or DDDR pacing mode.

It should be appreciated that the present invention may be utilized to suppress atrial tachyarrhythmias and may in general be incorporated into an anti-tachyarrhythmia system including specific high rate pacing and cardioversion shock therapies for providing staged therapies to treat a diagnosed arrhythmia.

Figure 1:
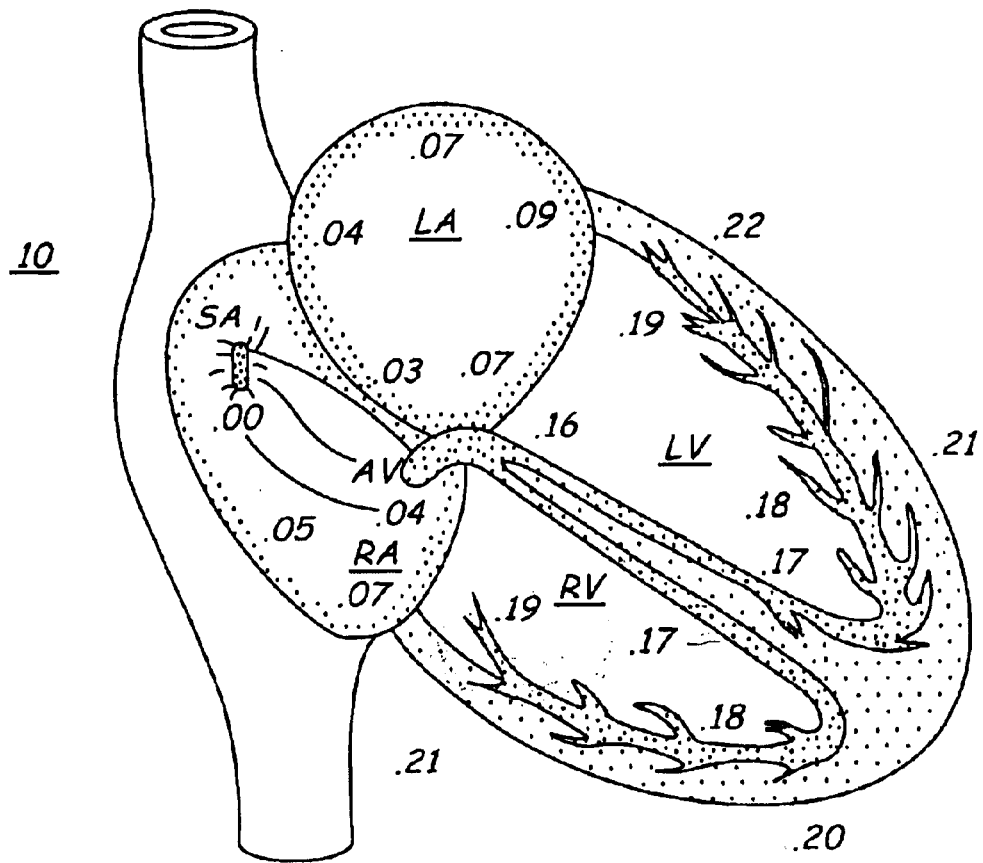
FIG. 1 is an illustration of transmission of the cardiac depolarization waves through the heart in a normal electrical activation sequence.

FIG. 1 is an illustration of transmission of the cardiac depolarization waves through the right atrium (RA), left atrium (LA), right ventricle (RV) and left ventricle (LV) of heart 10 in a normal electrical activation sequence at a normal heart rate with the conduction times exhibited thereon in seconds as described in the above-referenced '324 patent. The cardiac cycle commences normally with the generation of the depolarization impulse at the Sino-Atrial (SA) Node in the right atrial wall and its transmission through the atrial conduction pathways of Bachmann's Bundle and the Internodal Tracts at the atrial level into the left atrial septum. The RA depolarization wave reaches the Atrio-ventricular (AV) node and the atrial septum within about 40 msec and reaches the furthest walls of the RA and LA within about 70 msec, and the atria complete their contraction as a result. The aggregate RA and LA depolarization wave appears as the P-wave of the PQRST complex when sensed across external ECG electrodes and displayed. The component of the atrial depolarization wave passing between a pair of unipolar or bipolar pace/sense electrodes, respectively, located on or adjacent the RA or LA is also referred to as a sensed P-wave. Although the location and spacing of the external ECG electrodes or implanted unipolar atrial pace/sense electrodes has some influence, the normal P-wave width does not exceed 80 msec in width as measured by a high impedance sense amplifier coupled with such electrodes. A normal near field P-wave sensed between closely spaced bipolar pace/sense methods described herein in detail can be implanted and employed in treatment of an electrical conduction disturbance in a single heart chamber or between two heart chambers.

It will also be understood that the present invention can be implemented in the context of a dual chamber pacing system or pacemaker operating in a DDD or DDDR pacing mode.

It should be appreciated that the present invention may be utilized to suppress atrial tachyarrhythmias and may in general be incorporated into an anti-tachyarrhythmia system including specific high rate pacing and cardioversion shock therapies for providing staged therapies to treat a diagnosed arrhythmia.

FIG. 1 is an illustration of transmission of the cardiac depolarization waves through the right atrium (RA), left atrium (LA), right ventricle (RV) and left ventricle (LV) of heart 10 in a normal electrical activation sequence at a normal heart rate with the conduction times exhibited thereon in seconds as described in the above-referenced '324 patent. The cardiac cycle commences normally with the generation of the depolarization impulse at the Sino-Atrial (SA) Node in the right atrial wall and its transmission through the atrial conduction pathways of Bachmann's Bundle and the Internodal Tracts at the atrial level into the left atrial septum. The RA depolarization wave reaches the Atrio-ventricular (AV) node and the atrial septum within about 40 msec and reaches the furthest walls of the RA and LA within about 70 msec, and the atria complete their contraction as a result. The aggregate RA and LA depolarization wave appears as the P-wave of the PQRST complex when sensed across external ECG electrodes and displayed. The component of the atrial depolarization wave passing between a pair of unipolar or bipolar pace/sense electrodes, respectively, located on or adjacent the RA or LA is also referred to as a sensed P-wave. Although the location and spacing of the external ECG electrodes or implanted unipolar atrial pace/sense electrodes has some influence, the normal P-wave width does not exceed 80 msec in width as measured by a high impedance sense amplifier coupled with such electrodes. A normal near field P-wave sensed between closely spaced bipolar pace/sense electrodes and located in or adjacent the RA or the LA has a width of no more than 60 msec as measured by a high impedance sense amplifier.

The depolarization impulse that reaches the AV Node is distributed inferiorly down the bundle of His in the intra-ventricular septum after a delay of about 120 msec. The depolarization wave reaches the apical region of the heart about 20 msec later and is then travels superiorly though the Purkinje Fiber network over the remaining 40 msec. The aggregate RV and LV depolarization wave and the subsequent T-wave accompanying re-polarization of the depolarized myocardium are referred to as the QRST portion of the PQRST cardiac cycle complex when sensed across external ECG electrodes and displayed. The highest amplitude component of the QRS ventricular depolarization wave passing between a pair of unipolar or bipolar pace/sense electrodes, respectively, located on or adjacent the RV or LV is referred to as the sensed R-wave. Although the location and spacing of the external ECG electrodes or implanted unipolar ventricular pace/sense electrodes has some influence, the normal R-wave width does not exceed 80 msec in width as measured by a high impedance sense amplifier. A normal near field R-wave sensed between closely spaced bipolar pace/sense electrodes and located in or adjacent the RV or the LV has a width of no more than 60 msec as measured by a high impedance sense amplifier.

This normal electrical activation sequence becomes highly disrupted in patients suffering from advanced congestive heart failure and exhibiting IACD, LBBB, RBBB, and/or IVCD. These conduction defects exhibit great asynchrony between the RV and the LV due to conduction disorders along the Bundle of His, the Right and Left Bundle Branches or at the more distal Purkinje Terminals. Typical intra-ventricular peak—peak asynchrony can range from 80 to 160 msec or longer. In RBBB and LBBB patients, the QRS complex is widened far beyond the normal range to from >120 msec to 250 msec as measured on surface ECG. This increased width demonstrates the lack of synchrony of the right and left ventricular depolarizations and contractions.

In accordance with certain embodiments of the present invention, methods and apparatus are provided to restore the depolarization sequence of FIG. 1 and the synchrony between the right and left, atrial and ventricular heart chambers that contributes to adequate cardiac output. This restoration is effected through providing optimally timed cardiac pacing pulses to each heart chamber as necessary and to account for the particular implantation sites of the pace/sense electrodes in relation to each heart chamber.

As noted above, it has been common in the prior art to use very high impedance P-wave and R-wave sense amplifiers to amplify the low amplitude current or voltage difference signal that is generated across the pace/sense electrodes by the passage of a cardiac depolarization. The high impedance sense amplifiers use high gain to amplify the low amplitude signals and rely on pass band filters, time domain filtering and amplitude threshold comparison to discriminate a P-wave or R-wave from background electrical noise. Moreover, the sense amplifiers are uncoupled from the pace/sense electrodes during blanking periods of up to 100 msec after delivery of a pacing pulse to any of the pace/sense electrodes of the pacing system to avoid saturation of the sense amplifiers.

The present invention as described hereafter preferably uses isolated current replicators between the pair of pace/sense electrodes and the inputs of the sense amplifier to be able to shorten the applied blanking periods and to time out a relatively short $CDW^S$ and $CDW^P$ if they are employed or enabled in the pacing system Right and left heart chamber sense amplifier blanking intervals can be shortened to about the width of the pacing pulses which is typically 0.5–1.0 msec and up to about 10 msec. The blanking intervals can be minimized because of the ability of the isolated current replicators to block after potentials caused by a pacing pulse artifact reflected across the pace/sense electrode pair and to detect any closely following cardiac depolarization wavefront. Preferably, the blanking intervals are programmable so that they can be tailored after implantation and minimized to reflect the cardiac conduction conditions of the patient's heart.

Figure 2:
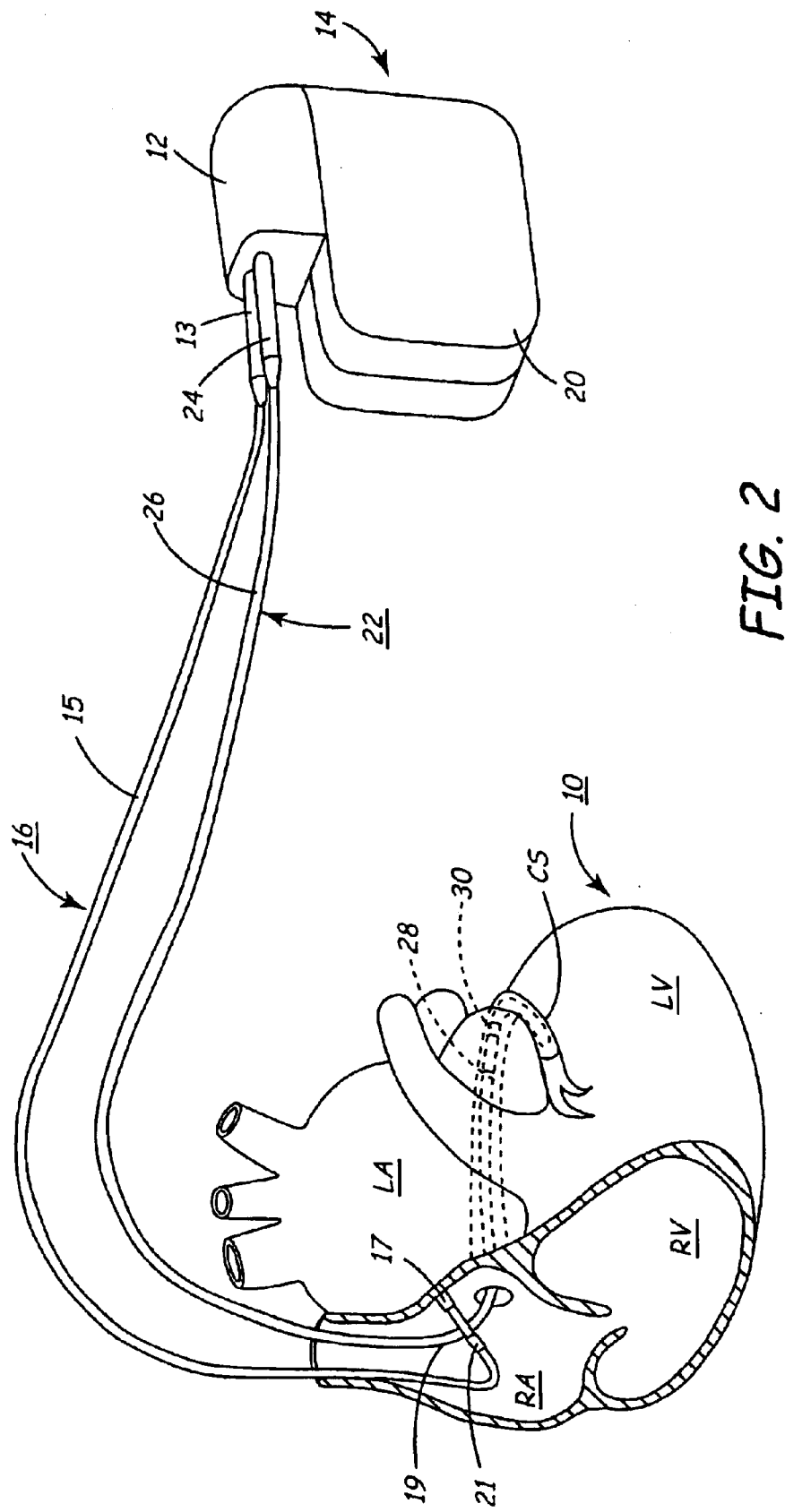
FIG. 2 is a schematic diagram depicting a two chamber, bi-atrial pacing system in which the present invention is implemented.

FIG. 2 is a schematic representation of an implanted, two chamber cardiac pacemaker of the above noted types for restoring synchronous contractions of the right and left atria. In FIG. 2, heart 10 includes the upper heart chambers, the right atrium (RA) and left atrium (LA), and the lower heart chambers, the right ventricle (RV) and left ventricle (LV) and the coronary sinus (CS) extending from the opening in the right atrium laterally around the atria to form the great vein that extends further inferiorly into branches of the great vein. The pacemaker IPG 14 is implanted subcutaneously, between the skin and the ribs. Bipolar, endocardial RA lead 16 and bipolar endocardial LA CS lead 22 are passed through a vein into the RA chamber of the heart 10 and into the CS to extend alongside the LA chamber. The RA lead 16 is formed with an in-line connector 13 fitting into a bipolar bore of IPG connector block 12 that is coupled to a pair of electrically insulated conductors within lead body 15 and connected with distal tip RA pace/sense electrode 19 and proximal ring RA pace/sense electrode 21. The distal end of the RA lead 16 is attached to the RA wall by an attachment mechanism 17. The LA CS lead 22 is formed with an in-line connector 24 fitting into a bipolar bore of IPG connector block 12 that is coupled to a pair of electrically insulated conductors within lead body 26 and connected with distal ring LA CS pace/sense electrode 30 and proximal ring LA CS pace/sense electrode 28. The distal end of the LA CS lead 26 is extended into the CS to position the LA CS pace/sense electrodes optimally with respect to the adjacent LA wall.

In operation, a P-wave sensed across either pair or one selected pair of the atrial pace/sense electrodes 17, 19 or 28, 30, is employed to reset the current A—A atrial escape interval and to start time out of an atrial sense event trigger CDW ($CDW^{S)}$. The A—A escape interval is typically timed from the right atrial paced and sensed events, but it can the left atrial paced and sensed events in appropriate circumstances. The right and left atrial sense $CDW^S$ lengths in msec are programmed to reflect the normal conduction delays of spontaneous atrial depolarizations between the atrial pace/sense electrodes 17, 19 and 28, 30 in a normal electrical activation sequence or to respond to a reverse activation sequence. An atrial pace pulse is delivered to the other pair of atrial pace/sense electrodes 17, 19 or 28, 30 to synchronize the right and left atrial depolarizations if the appropriate atrial $CDW^S$ times out without the sensing of the P-wave at that other pair of the pace/sense electrodes. If the A—A atrial escape interval times out, then the atrial pace pulse is typically first delivered across the RA pace/sense electrodes 17, 19, and time-out of a paced atrial CDW ($CDW^{P)}$ is commenced. An atrial pace pulse is delivered to the LA CS pace/sense electrodes 28, 30 if the paced atrial $CDW^P$ times out without the sensing of the P-wave at the LA CS pace/sense electrodes 28 and 30.

Figure 3:
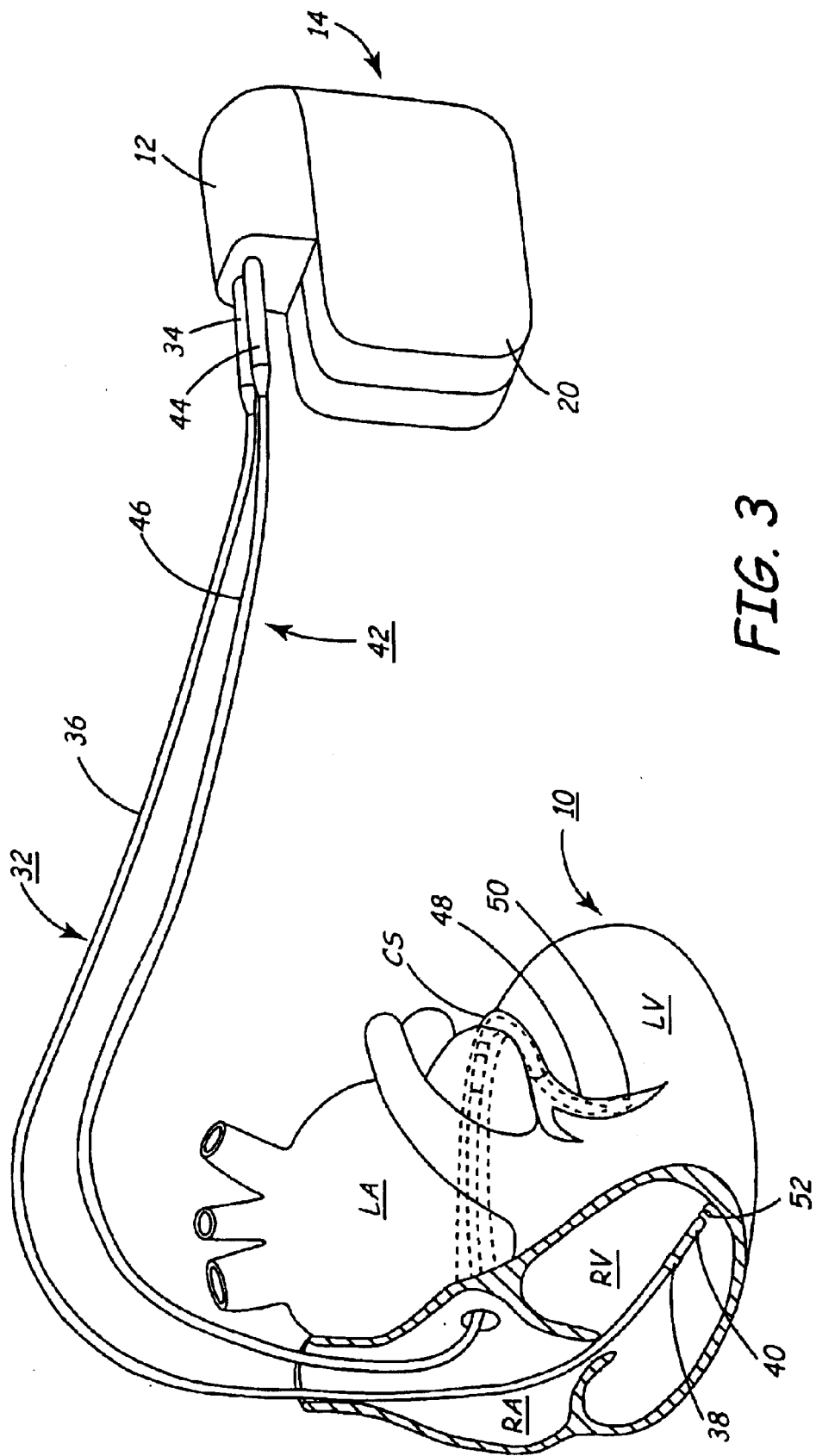
FIG. 3 is a schematic diagram depicting a two chamber, bi-ventricular pacing system in which the present invention is implemented.

FIG. 3 is a schematic representation of an implanted, two chamber cardiac pacemaker of the above noted types for restoring synchronous contractions of the right and left ventricles. Bipolar, endocardial LV CS lead 42 is passed through a vein into the RA chamber of the heart 10, into the CS and then inferiorly in the great vein and cardiac veins extending therefrom to extend the distal ring pace/sense electrodes 48 and 50 alongside the LV chamber. Bipolar, endocardial RV lead 32 is passed through the vein into the RA chamber of the heart 10 and into the RV where its distal ring and tip pace/sense electrodes 38 and 40 are fixed in place in the apex or in the inter-ventricular septum by a distal attachment mechanism 52. The RV lead 32 is formed with an in-line connector 34 fitting into a bipolar bore of IPG connector block 12 that is coupled to a pair of electrically insulated conductors within lead body 36 and connected with distal tip pace/sense electrode 40 and proximal pace/sense ring electrode 38. The LV CS lead 42 is formed with an in-line connector 44 fitting into a bipolar bore of IPG connector block 12 that is coupled to a pair of electrically insulated conductors within lead body 46 and connected with distal ring pace/sense electrode 50 and proximal pace/sense ring electrode 48. The distal end of the LV CS lead 42 is extended into the CS to position the ring electrodes optimally with respect to the adjacent LV wall.

In operation, the R-wave sensed across one selected pair of the ventricular chamber pace/sense electrodes 38, 40 or 48, 50 is employed to reset the current V—V ventricular escape interval and to start time-out of a ventricular $CDW^S$. The V—V escape interval is typically timed from RV paced and sensed events, but it can be timed from LV paced and sensed events in appropriate circumstances. The right and left ventricular $CDW^S$ lengths in msec are programmed to reflect the normal conduction delays between the ventricular pace/sense electrodes 38, 40 and 48, 50 in a normal electrical activation sequence and in a reverse activation sequence. A ventricular pace pulse is delivered to the other pair of ventricular pace/sense electrodes to synchronize the right and left ventricular depolarizations if the right or left ventricular $CDW^S$ times out without the sensing of the R-wave at the other pair of the pace/sense electrodes 38, 40 or 48, 50. If the V—V ventricular escape interval does time out, then the ventricular pace pulse is typically first delivered across the RV pace/sense electrodes 38 and 40, and the ventricular pace $CDW^P$ is commenced. A ventricular pace pulse is delivered to the LV CS pace/sense electrodes 48 and 50 if the ventricular $CDW^P$ times out without the sensing of the R-wave at the LV CS pace/sense electrodes 48 and 50. As described further below, this order can be reversed in appropriate instances.

These illustrated RA and LA and RV and LV pace/sense leads and electrode locations are merely exemplary of possible leads and electrode locations that can be employed in the practice of these embodiments of the present invention. It will be understood that one or more of the other types of endocardial and epicardial leads and pace/sense electrodes located in or about the right and left chambers of the heart can be substituted for those illustrated in FIGS. 2 and 3 and described above.

Figure 4:
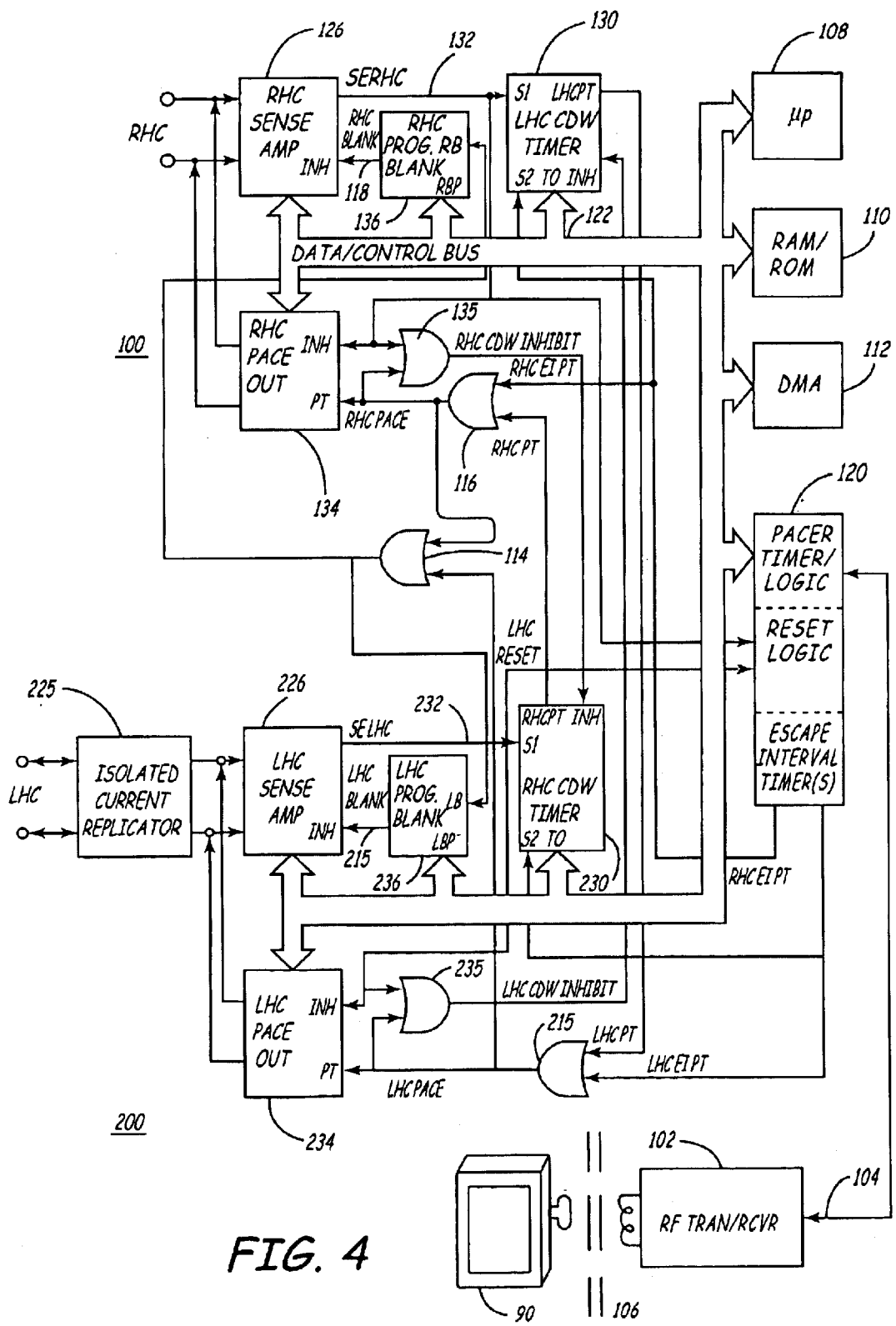
FIG. 4 is a simplified block diagram of the circuitry of the present invention for the right and left heart chamber, IPG employed in the systems of FIGS. 2 and 3.

In FIG. 4, the RHC and LHC designations are employed to embrace both bi-atrial and bi-ventricular contexts of use of a two chamber pacing system of the present invention. Thus, FIG. 4 is a simplified block diagram of a two chamber pacing system circuit comprising RHC circuitry 100 and LHC circuitry 200 and common components that can be employed to provide the pacing and sensing functions in a two chamber, bi-atrial, pacemaker of FIG. 2 or bi-ventricular pacemaker of FIG. 3. Timing and control of the RHC and LHC circuitry 100 and 200 is realized through the software routines maintained in a microcomputer comprising the microprocessor 108, RAM/ROM chip 110, and DMA circuit 112 and in a pacer timing/logic circuit 120 coupled therewith. Operating modes and parameter values are programmed into RAM in RAM/ROM chip 110 through use of the external programmer 90 that transmits RF telemetry transmissions through the patient's skin to an antenna 106 and the RF telemetry transmitter/receiver 102 coupled with pacer timing/logic circuit 120. Such transcutaneous RF telemetry is well known in the art and allows programming of the operating modes, the A—A and V—V escape intervals and other timing and control intervals including the left and right chamber $CDW^S$ and $CDW^P$ time lengths in accordance with the present invention.

Interconnections are provided between the RHC and LHC pacing and sensing circuitry 100 and 200 to perform the timing out of each $CDW^S$ and pacing if necessary to assure that the right and left heart chambers are depolarized and contract in the desired time relation to one another. The two chamber IPG circuit of FIG. 4 is intended to comprehensively illustrate particular bi-atrial and bi-ventricular IPG circuits that may be employed to practice the various embodiments of the invention. The depicted RHC and LHC pacing and sensing circuitry 100 and 200 is fully symmetric. It will be understood that asymmetric two chamber IPG circuits can be derived from the comprehensive two chamber IPG circuit illustrated in FIG. 4 that function to treat unduly prolonged RHC-to-LHC conduction delays or LHC-to-RHC conduction delays. Such asymmetric two chamber IPG circuits can be effected either by selectively disabling (through programming commands) or by simply physically eliminating unused components of the RHC or LHC circuitry 100 or 200. The components and logical interconnections illustrated in FIG. 4 are first described, and then the possible modifications are described.

With respect to the RHC circuitry 100, the RHC pace/sense terminals in the connector block 12 are coupled to the input terminals of RHC sense amplifier 126 and to the output terminals of the RHC pacing pulse output circuit 134. Operating parameters of the RHC sense amplifier 126 and the RHC pacing pulse output circuit 134 are set by programmed parameter values and operating modes provided on data/control bus 122. The RHC pacing pulse output circuit 134 delivers an RHC pacing pulse to the RHC terminals at a programmed pulse width and amplitude in response to an RHC PACE signal that is passed through OR gate 116. The RHC PACE signal is either the RHC pace trigger (RHC PT) signal generated by the RHC CDW timer 230 or the RHC escape interval pace trigger (RHC EI PT) signal generated by the escape interval timer in pacer timing/logic circuit 120.

An RHC BLANK signal is applied on line 118 to the RHC sense amplifier 126 that provides an RHC blanking period during pacing pulse delivery and for a short period of less than about 100 msec following delivery of an RHC pacing pulse or of less than about 7 msec following delivery of an LHC pacing pulse. The RHC BLANK signal is provided by RHC blanking circuit 136 in response to an RHC blanking trigger signal passed through OR gate 114 to the RB input. The OR gate 114 provides the RHC BLANK AND LHC BLANK trigger signals when a pacing pulse is triggered and delivered by either of the RHC and LHC pace output circuits 134 and 234. The OR gate 114 passes the RHC PACE and LHC PACE output signals of OR gate 116 and OR gate 216 which in turn pass the RHC pace trigger (RHC PT) and LHC pace trigger (LHC PT) signals that are generated by the time out of the escape interval or the programmable $CDW^S$ and $CDW^P$ times. The duration of the RHC BLANK signal is programmed into RAM/ROM chip 110 and retrieved and applied on data/control bus 122 to the RBP input of the programmable RHC blanking circuit 136. The RHC sense amplifier 126 is thereby rendered incapable of responding to an RHC depolarization signal during the short time that an RHC BLANK signal is applied to it on line 118.

It will be understood that the RHC programmable blanking circuit 136 shown schematically in FIG. 4 can be configured to operate to disconnect the sense amplifier inputs from the RHC lead conductors in the manner described above.

When the RHC BLANK signal is not present, the RHC sense amplifier 126 responds to an RHC cardiac depolarization by providing a high amplitude, short duration, sensed event RHC (SERHC) signal on line 132. The RHC sense amplifier 126 responds to an RHC cardiac depolarization sensed across the RHC pace/sense electrodes. The RHC cardiac depolarization can originate spontaneously in the RHC or can originate spontaneously in the LHC or be evoked by an LHC pace pulse delivered to the LHC pace/sense electrodes and, in either case, be conducted to the RHC pace/sense electrodes in the RHC. The SERHC signal is provided to the programmable LHC CDW timer 130 to start timing out the programmed LHC $CDW^S$ time if the LHC CDW timer 130 is not inhibited at the time. The SERHC signal is also applied to the RHC inhibit input of the RHC pacing output circuit 134 to prevent it from operating and to the reset logic within pacer timing/logic circuit 120 to reset the escape interval timer. The escape interval timer is restarted by either the SERHC signal or the SELHC signal to generate either the RHC EI PT signal or the LHC escape interval pace trigger (LHC EI PT) signal on its expiration. The SERHC signal is also passed through the NOR gate 135 as the RHC CDW INHIBIT signal to reset and inhibit the RHC CDW timer as described below.

The LHC $CDW^S$ and $CDW^P$ time lengths are programmed into RAM/ROM chip 110 and retrieved and applied on data/control bus 122 to the TD input to the programmable LHC CDW timer 130. The programmable LHC CDW timer 130 starts timing out the programmed LHC $CDW^S$ time on receipt of the SERHC signal at start input S1. In addition, the programmable LHC CDW timer 130 starts timing out the programmed LHC $CDW^S$ time at the time that the RHC PACE signal is applied to the start input S2 of RHC pacing output circuit 134. It will be understood that the LHC CDW timer 130 may include redundant timers and selection logic to provide that a first LHC $CDW^S$ time may be started upon application of the SERHC signal at start input S1 and a second LHC $CDW^P$ time may be started upon application of the RHC EI PT signal to the start input S2. It will also be understood that the LHC CDW timer 130 may include programmable logic that responds to a programmed in selection command to disable response of the LHC CDW timer 130 to one or both of the SERHC and the RHC EI PT signals.

The programmable LHC CDW timer 130 generates an LHC PT signal if the LHC sense amplifier 226 does not detect an LHC depolarization wave and generate the left heart chamber sensed event signal (SELHC) and LHC RESET command on line 232 before the programmed RHC $CDW^S$ or $CDW^P$ is timed out. The LHC PT signal is applied through OR gate 216 to the LHC PACE input of the LHC pacing pulse output circuit 234 which provides an LHC pacing pulse to the LHC terminals of the connector assembly 12. In this manner, the LHC pacing pulse is applied to the LHC terminals of the connector assembly 12 following the lapse of the LHC $CDW^P$ or $CDW^S$ following an RHC pacing pulse or a SERHC signal, respectively, to restore RHC-to-LHC synchrony.

The timing out of the programmable LHC $CDW^S$ or $CDW^P$ time by the LHC CDW timer 130 is halted and further triggering of the LHC timer 130 is inhibited by an LHC CDW INHIBIT signal applied to the inhibit (INH) input of LHC CDW timer 130. The LHC CDW INHIBIT signal is of a duration that is longer than any programmed CDW time but shorter than the pacing escape interval. The LHC CDW INHIBIT signal prevents the LHC CDW timer 130 from being restarted in response to a SERHC signal generated on sensing a depolarization that is conducted from the LHC pace/sense electrodes to the RHC pace/sense electrodes that is itself evoked by the LHC PT signal that it delivered to NOR gate 216. Consequently, the LHC PT signal is passed through the NOR gates 216 and 235 and applied to the INH input of LHC CDW timer 130. Similarly, the LHC CDW INHIBIT signal is generated by passage of the LHC EI PT signal or the SELHC signal through NOR gate 235 and applied to the INH input of the LHC CDW timer. Only the RHC CDW timer 230 should be started when these RHC paced and sensed events occur.

The LHC signal sensing and pacing output circuitry 200, in conjunction with NOR gates 114, 116 and 135, is configured and functions in a mirror image fashion to the RHC signal sensing and pacing output circuitry 100 described above. However, in this case, an isolated current replicator circuit or replicator 225 illustrated in FIGS. 8 and 9 and described further below is interposed between the LHC pace/sense electrode pair and the inputs of the LHC sense amplifier 226 as well as the outputs of the LHC pacing output circuit 234 of the LHC pacing channel. The LHC pace/sense terminals in the connector block 12 are coupled via capacitive filtered feedthroughs through the IPG case to the output current loop of the isolated current replicator 225. The input current loop is coupled with both the input of the LHC sense amplifier 226 and the output of the pacing output circuit 234. In this embodiment, pacing trigger pulses delivered to the input current loop are replicated in the output current loop and delivered to the LHC pace/sense electrodes, whereas cardiac signals traversing the LHC pace/sense electrodes and the output current loop are replicated in the input current loop and provided to the LHC sense amplifier 234.

It will be understood that the LHC programmable blanking circuit 236 shown schematically in FIG. 4 can be configured to operate to disconnect the sense amplifier inputs from the input current loop of the isolated current replicator 225 employing blanking switches of the types described above. Therefore, it will be understood that the input current loop of the isolated current replicator circuit 225 can be applied to the inputs of the LHC sense amplifier 226 through such blanking switches operated by the LHC programmable blanking circuit 236.

Moreover, it will be understood that a pair of isolated current replicators could be interposed in the LHC pacing channel. A first isolated current replicator can be interposed to isolate the LHC pace/sense electrode pair of the LHC pacing channel from the LHC sense amplifier 226. A second isolated current replicator can be interposed to isolate the LHC pace/sense electrode pair of the LHC pacing channel from the LHC pacing output circuit 234.

An LHC BLANK signal is applied on line 218 to the LHC sense amplifier 226 during the RHC PACE or LHC PACE signal as reflected through OR gate 114 and optionally for a blanking time period thereafter. The LHC blanking period provided by the LHC BLANK signal is preferably of less than about 7 msec following delivery of an RHC pacing pulse or of less than about 100 msec following delivery of an LHC pacing pulse. The LHC BLANK signal is provided by LHC blanking circuit 236 in response to an RHC blanking trigger signal generated by OR gate 114 and applied to the LB input. The duration of the LHC BLANK signal is programmed into RAM/ROM chip 110 and retrieved and applied on data/control bus 122 to the LBP input of the programmable LHC blanking circuit 236.

As in the case of the LHC CDW timer 130, it will be understood that the RHC CDW timer 230 includes redundant timers and selection logic to time the sense RHC CDW$^S$ started upon application of the SELHC signal at start input S1 and a pace RHC CDW$^P$ started upon application of the LHC EI PT signal to the start input S2. The programmable RHC CDW timer 230 starts timing out the programmed RHC CDW$^P$ time at the time that the LHC PACE signal is applied to the LHC pacing output circuit 234 if it is not inhibited. It will also be understood that the RHC CDW timer 230 may include programmable logic that responds to a programmed in selection command to disable response of the RHC CDW timer 230 to one or both of the SELHC and the LHC EI PT signals.

The LHC sense amplifier 226 responds to an LHC cardiac depolarization sensed across the LHC pace/sense electrodes when it is not blanked by an LHC BLANK signal by providing a high amplitude, short duration sensed event signal SELHC on line 232. The LHC cardiac depolarization can originate spontaneously in the LHC or can originate spontaneously in the RHC or be evoked by an RHC pace pulse delivered to the RHC pace/sense electrodes and, in either case, be conducted to the LHC pace/sense electrodes in the LHC. The SELHC signal is provided to the S1 input of programmable RHC CDW$^S$ timer 230 to start timing out the programmed RHC CDW$^S$ time if it is not inhibited at the time. The SELHC signal is also applied to the LHC INH input of the LHC pacing output circuit 234 to prevent it from operating and to the reset logic within pacer timing/logic circuit 120 to reset the escape interval timer if the escape interval timer is programmed to respond to it. The SELHC signal is also applied as the INH input of the LHC CDW timer 130 through NOR gate 235, although it is not actually timing out an LHC CDW time in this scenario.

The programmable RHC CDW timer 230 generates an RHC PT signal at the time out of the RHC CDW$^S$, if the RHC sense amplifier 126 does not earlier detect an RHC depolarization wave and generate the SERHC signal. The RHC PT signal is applied through OR gate 116 to the RHC PACE input of the RHC pacing pulse output circuit 134 which provides a pacing pulse to the RHC pace/sense terminals of the connector assembly 12. However, if the SERHC signal is generated during the RHC CDW$^S$ time, it resets the RHC CDW timer 230 to terminate the RHC CDW time and inhibits the operation of the RHC CDW timer 230 from being restarted for a preset inhibition period in the manner described above.

The sensing characteristics of the RHC and LHC sense amplifiers 126 and 226, the CDW$^S$ and CDW$^P$ times of the LHC and RHC CDW timers 130 and 230 and the RHC and LHC pacing pulse output circuits 134 and 234 can be separately programmed. The external programmer 90 is employed to provide the programmed modes and values via downlink telemetry with antenna 106 and RF transmitter/receiver 102 that are decoded and stored in RAM/ROM chip 110 in a manner well known in the art. Thus, while there is symmetry in the right and left heart chamber pacing and sensing circuitry, the operation can be made symmetric or asymmetric to optimize function in a given patient.

In the illustrated comprehensive two chamber IPG circuit of FIG. 4, a single escape interval timer can be programmed with an escape interval value and programmed to generate the RHC EI PT signal or the LHC EI PT at the time out of the escape interval unless the escape interval is earlier restarted by a sensed RHC or LHC depolarization.

The normally functioning heart involves the depolarization and contraction of the right atrium first, the left atrium second and the right and left ventricles after the AV delay time as shown above with respect to FIG. 1. The inter-atrial conduction disturbances involve either a prolonged delay that may approach or exceed the AV delay or a complete dissociation of the right and left atrial contractions at all or certain heart rates. The inter-ventricular conduction disturbances typically involve a retardation of the depolarization wave through the left ventricle outer wall which may be caused by damage to the conduction system and/or an enlarged heart muscle found in congestive heart chamber. Whatever the cause, in the typical case to be treated, the right heart chamber(s) contracts first, followed by the contraction of the left heart chamber(s) after the prolonged conduction delay. The converse situation does not arise typically but can occur as a result of premature atrial contractions arising in the left atrium. Thus, in this case, the IPG circuit of FIG. 4 can be programmed to operate in an asymmetric manner wherein the use of the LHC CDW timer 230 and is programmed OFF by a programmed in command or is eliminated entirely.

For example, the two chamber IPG circuit components are capable of being programmed to respond to and treat unduly prolonged RHC-to-LHC conduction delays in the normal electrical activation sequence of FIG. 1 that occur due to IACD, LBBB, IVCD, RV ectopic foci conduction patterns, RV pacing conduction patterns. In these cases, programmed in mode commands disable the RHC CDW timer 230, and the reset logic is programmed to only employ the SERHC signal to reset the escape interval timer. In addition, the escape interval timer only generates the RHC EI PT signal.

However, it will be realized that the two chamber IPG circuit components are capable of being programmed to respond to and treat unduly prolonged LHC-to-RHC conduction delays in a reverse electrical activation sequence than the normal electrical activation sequence of FIG. 1 that occur due to RBBB, IVCD, LV ectopic foci conduction patterns, and LV pacing conduction patterns. In these cases, programmed in mode commands disable the LHC CDW timer 130, and the reset logic is programmed to only employ the SELHC signal to reset the escape interval timer. In addition, the escape interval timer only generates the LHC EI PT signal. Of course, these configurations can be realized through a physical reduction of the components and interconnections of the comprehensive two chamber pacing system of FIG. 4.

It should be noted that the above-described two chamber pacing system of FIG. 4 can also be employed as a multi-site pacing system where the RHC and LHC leads are actually introduced into a common heart chamber such that the pace/sense electrodes are separated from one another in that heart chamber. For example, it may be desirable to locate the RHC pace/sense electrodes in the RV apex and the LHC pace/sense electrodes affixed to the inter-ventricular septal wall in relation to the bundle of His to effect synchronized delivery of pacing pulses to these locations in the RV in a sequence depending upon the sequence of sensed ventricular depolarizations or R-waves at these sites. The present invention can be implemented into such a pacing system that provides two (or more) pacing/sensing channels in or in relation to a single heart chamber. Other variations on the configuration and operation of the pacing system of FIG. 4 and the following described embodiments appear below.

Figure 5:
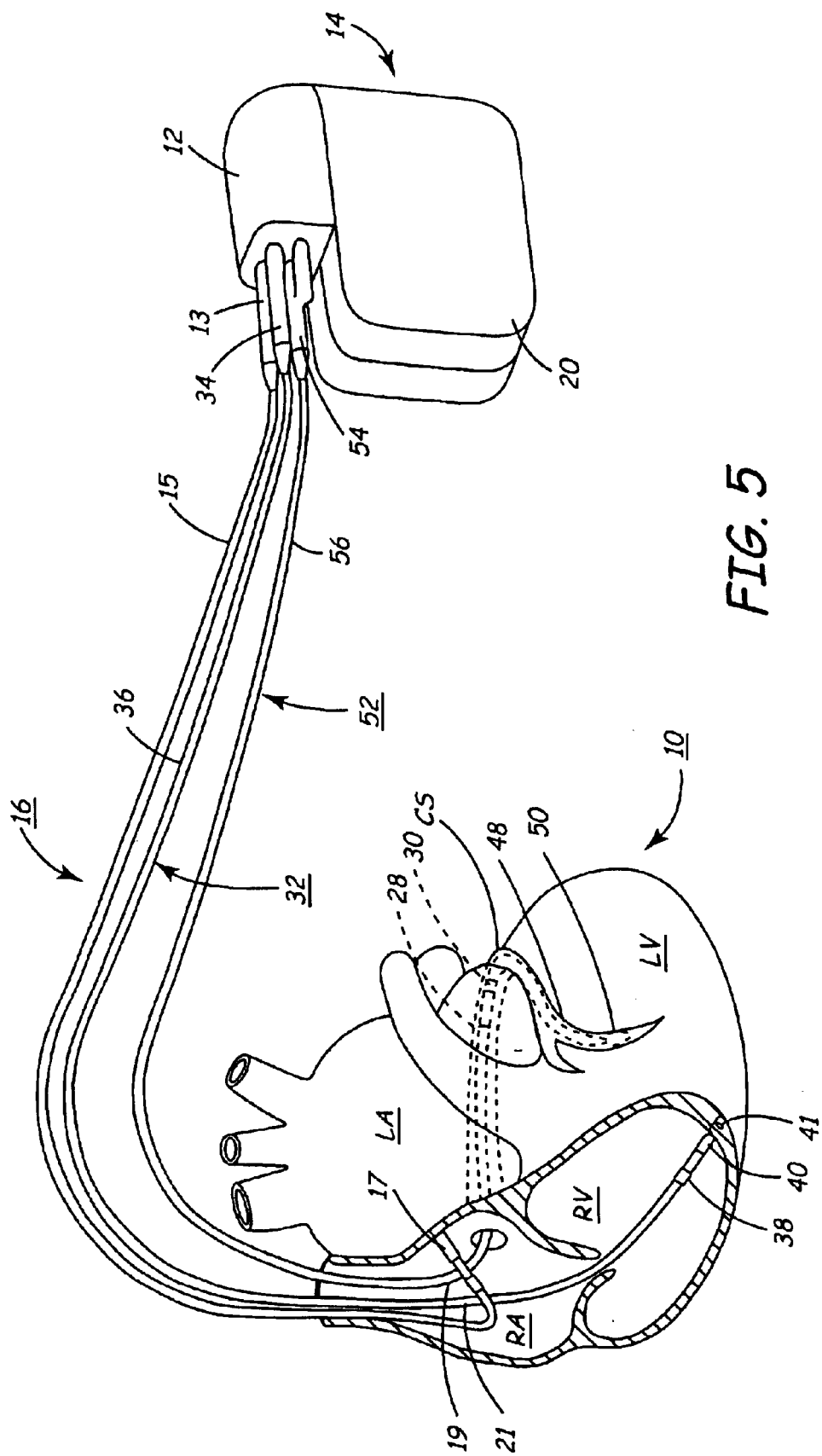
FIG. 5 is a schematic diagram depicting a three or four chamber, bi-atrial and/or bi-ventricular, pacing system in which the present invention is implemented.

FIG. 5 is a schematic representation of an implanted, four chamber cardiac pacemaker of the above noted types for restoring synchronous contractions of the right and left atria and the right and left ventricles. The in-line connector 13 of RA lead 16 is fitted into a bipolar bore of IPG connector block 12 and is coupled to a pair of electrically insulated conductors within lead body 15 that are connected with distal tip RA pace/sense electrode 19 and proximal ring RA pace/sense electrode 21. The distal end of the RA lead 16 is attached to the RA wall by a conventional attachment mechanism 17. Bipolar, endocardial RV lead 32 is passed through the vein into the RA chamber of the heart 10 and into the RV where its distal ring and tip RV pace/sense electrodes 38 and 40 are fixed in place in the apex by a conventional distal attachment mechanism 41. The RV lead 32 is formed with an in-line connector 34 fitting into a bipolar bore of IPG connector block 12 that is coupled to a pair of electrically insulated conductors within lead body 36 and connected with distal tip RV pace/sense electrode 40 and proximal ring RV pace/sense electrode 38.

In this case, a quadripolar, endocardial LV CS lead 52 is passed through a vein into the RA chamber of the heart 10, into the CS and then inferiorly in the great vein to extend the distal pair of LV CS pace/sense electrodes 48 and 50 alongside the LV chamber and leave the proximal pair of LA CS pace/sense electrodes 28 and 30 adjacent the LA. The LV CS lead 52 is formed with a four conductor lead body 56 coupled at the proximal end to a bifurcated in-line connector 54 fitting into a pair of bipolar bores of IPG connector block 12. The four electrically insulated lead conductors in LV CS lead body 56 are separately connected with one of the distal pair of LV CS pace/sense electrodes 48 and 50 and the proximal pair of LA CS pace/sense electrodes 28 and 30.

In operation, a P-wave sensed across the RA pace/sense electrodes 17 and 19 or the LA pace/sense electrodes 28 and 30 during the V-A escape interval timed from a preceding ventricular pacing pulse or R-wave sensed event is employed to start an AV delay and to start an LA $CDW^S$ or an RA $CDW^S$, respectively. An atrial pace pulse is delivered to the other pair of atrial pace/sense electrodes 17 and 19 or 28 and 30 if the respective LA or RA $CDW^S$ times out without the sensing of the same conducted P-wave at that other pair of the atrial pace/sense electrodes.

If the V-A atrial escape interval does time out without sensing a P-wave at either pair of atrial pace/sense electrodes 17 and 19 or 28 and 30, then the atrial pace pulse is typically first delivered across the RA pace/sense electrodes 17 and 19, and the respective LA $CDW^P$ time is commenced. Then, an atrial pace pulse is delivered to the LA CS pace/sense electrodes 28 and 30 only if the LA $CDW^P$ times out without the sensing of the P-wave at those pace/sense electrodes. However, it is also possible to program the reverse order of delivery so that the first atrial pace pulse is delivered to the LA CS pace/sense electrodes 28 and 30 at the expiration of the V-A atrial escape interval. Then, an atrial pace pulse is delivered to the RA pace/sense electrodes 17 and 19 only if the RA $CDW^P$ time times out without the sensing of the P-wave at the RA pace/sense electrodes.

It is possible in this embodiment to employ separate programmable sense AV (SAV) delays that are employed depending on whether the first atrial sensed event is sensed across the RA pace/sense electrodes 17 and 19 or the LA CS pace/sense electrodes 28 and 30. Moreover, it is possible to employ separate programmable paced AV (PAV) delays that are employed depending on whether the first atrial pacing pulsed is delivered across the RA pace/sense electrodes 17 and 19 or the LA CS pace/sense electrodes 28 and 30. These separately programmable SAV and PAV delays, denoted $SAV^{RA}$ and $PAV^{RA}$ and $SAV^{LA}$ and $PAV^{LA}$, can be programmed in length to provide the most physiologic AV delay between the particular locations of the RA and LA pace/sense electrodes and a selected one of the RV and LV pace/sense electrodes into account. This approach employing separate programmable $SAV^{RA}$ and $SAV^{LA}$ delays and separate programmable $PAV^{RA}$ and $PAV^{LA}$ delays is disclosed herein in reference to FIGS. 6 and 7 as one approach in which the present invention can be practiced. However, it will be understood that the present invention can be practiced employing a less complex approach using only a single, programmable AV delay or just one SAV delay and PAV delay.

Thus, in the preferred more complex case, a $SAV^{RA}$ or $SAV^{LA}$ or a $PAV^{RA}$ or $PAV^{LA}$ time is started on either sensing the first P-wave or on delivery of the first atrial pacing pulse to either the right or left atrial heart chamber. An R wave sensed across either of the RV or LV CS pace/sense electrodes 38 and 40 or 48 and 50 during the SAV or PAV time delay is employed to reset the AV timer, to start a V-A escape interval, and to start a respective LV $CDW^S$ or RV $CDW^S$. A ventricular pace pulse is delivered to the other pair of RV or LV CS pace/sense electrodes 38 and 40 or 48 and 50 if the LV $CDW^S$ or RV $CDW^S$ times out without the sensing of the R-wave at the other pair of the RV or LV CS pace/sense electrodes.

Assuming that the normal activation sequence is to be restored, a single AV delay corresponding to a normal AV conduction time from the AV node to the bundle of His is programmed for use. If the AV delay times out, then the ventricular pace pulse is typically programmed to be first delivered across the RV pace/sense electrodes 38 and 40, and an LV $CDW^P$ is commenced. A left ventricular pace pulse is programmed to be delivered to the LV CS pace/sense electrodes 48 and 50 if the LV $CDW^P$ times out without the sensing of the R-wave at the LV-CS pace/sense electrodes 48 and 50.

Then, the sequence is repeated such that if the V-A escape interval time out, then an RA pace pulse is typically first delivered across the RA pace/sense electrodes 17 and 19, the AV delay timer is restarted, and the LA CDW time is commenced. An LA pace pulse is delivered to the LA CS pace/sense electrodes 28 and 30 if the LA CDW time times out without the sensing of the P-wave at the LA CS pace/sense electrodes 28 and 30.

Each SAV and PAV delay and each $CDW^S$ and $CDW^P$ can be programmed to restore the normal activation sequence taking the particular conduction disturbance and the location of the RA, LA, RV and LV pace/sense electrode locations into account. The activation sequence can also be modified to time the AV delays and the atrial chamber $CDW^S$ and $CDW^P$ from initial LA depolarizations arising from LA ectopic foci.

Figure 6:
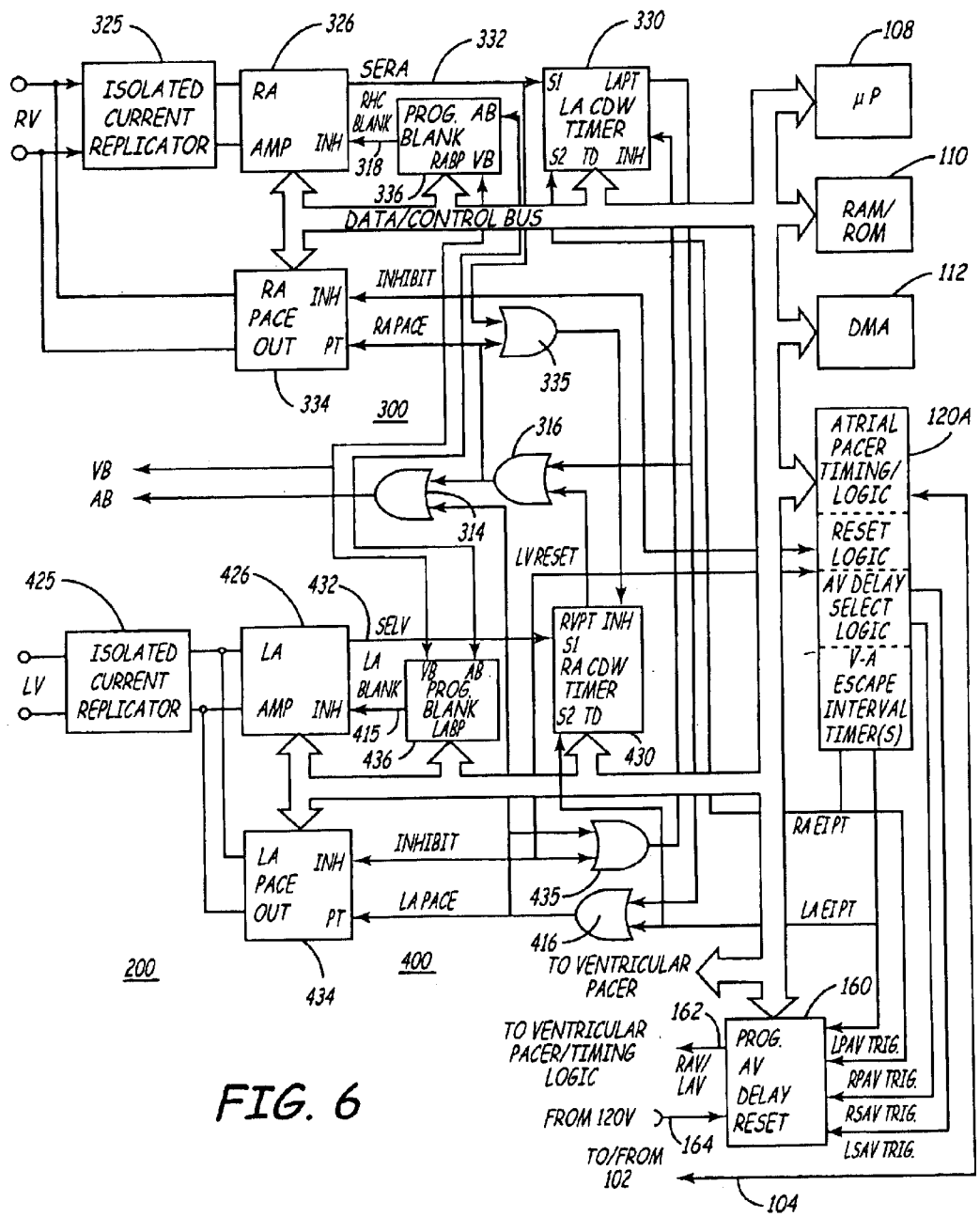
FIGS. 6 and 7 collectively are a simplified block diagrams of one embodiment of IPG circuitry of the present invention employed in the system of FIG. 5 for providing four pacing chambers or selectively programming three pacing chambers for selectively pacing right and left, upper and lower, heart chambers.
Figure 7:
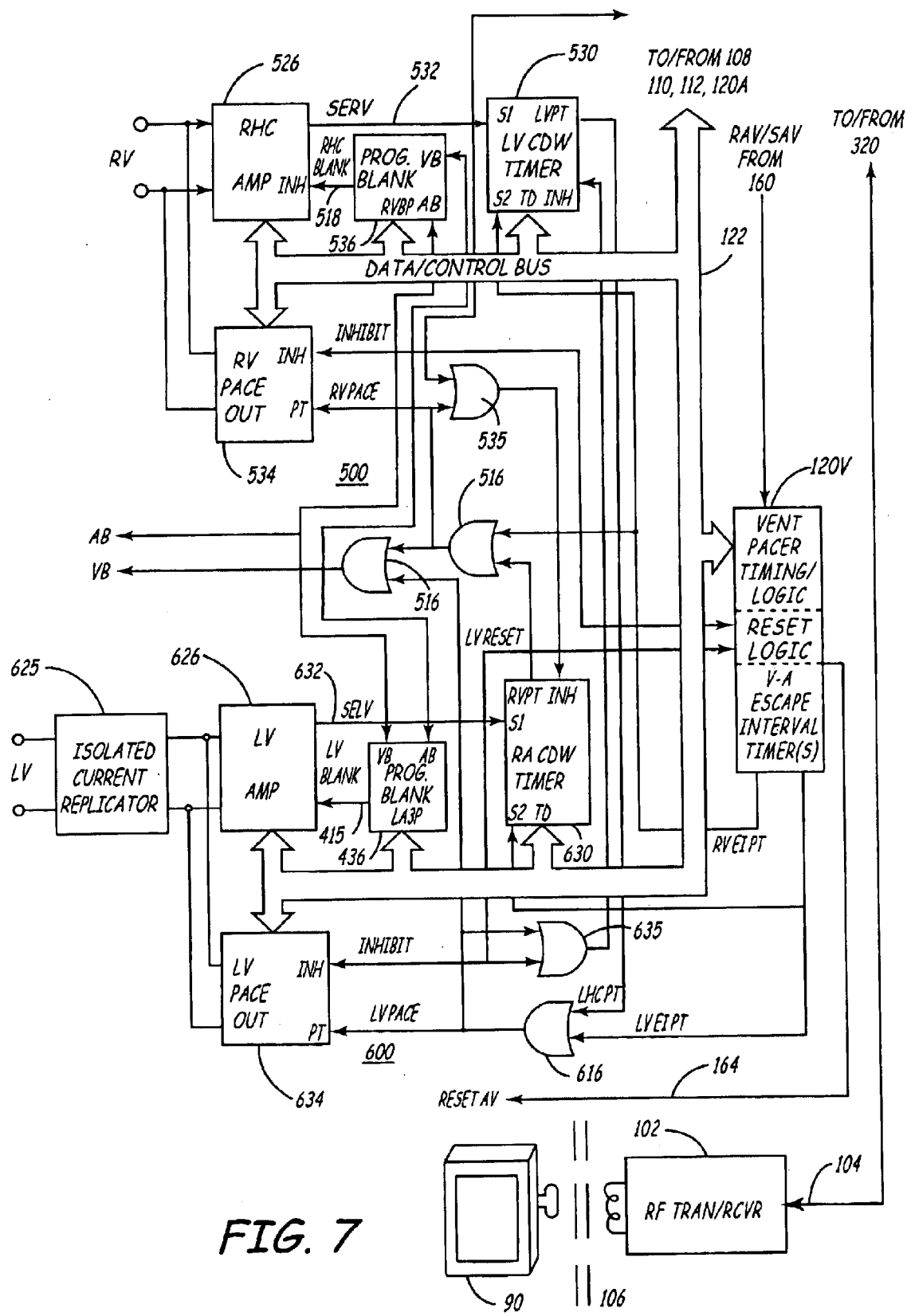

FIGS. 6 and 7 collectively comprise a simplified block diagram of a comprehensive, four chamber IPG circuit of the present invention for the right and left heart chamber, four chamber pacemaker IPG 14 employed in the system of FIG. 5. FIG. 6 illustrates the RA and LA pacing and sensing circuitry 300 and 400, respectively in relation to the data/control bus 122, the atrial pacer/timing logic circuit 120A, the microcomputer components 108, 110, 112 and the programmable AV delay logic 160. FIG. 7 illustrates the RV and LV pacing and sensing circuitry 500 and 600, respectively in relation to the data/control bus 122, the ventricular pacer/timing logic circuit 120V, the RF telemetry transmitter/receiver 102 and the external programmer 90. The microcomputer components 108, 110, 112 and the atrial pacer/timing logic circuit 120A of FIG. 6 are interconnected with the RV and LV pacing and sensing circuitry 500 and 600 and the ventricular pacer/timing logic circuit 120V of FIG. 7 via the data/control bus 122. The RF telemetry transmitter/receiver 102 of FIG. 7 is connected with the atrial pacer timing/logic circuit 120A of FIG. 6 via conductor 104, and the ventricular pace trigger output signal from programmable AV delay circuit 160 of FIG. 6 is coupled to the ventricular pacer/timing logic circuit 120V of FIG. 7 via the conductor 162. The atrial and ventricular pacer/timing logic circuit 120A and 120V and the programmable AV delay circuit 160 may alternatively be combined in a common circuit, as is conventional in DDD pacemakers.

The RA and LA pacing and sensing channels 300 and 400 and the RV and LV pacing and sensing channels 500 and 600 generally each follow the architecture of the RHC and LHC circuitry 100 and 200 of FIG. 4 described above in detail. The blanking circuitry differs somewhat in this four chamber embodiment to allow for the blanking of all four of the RA, LA, RV and LV sense amplifiers 326, 426, 526, 626 in response to delivery of a pace pulse by any of the RA, LA, RV and LV pace output circuits 334, 434, 534, 634. Each of the RA, LA, RV and LV programmable blanking circuits 336, 436, 536 and 636 generates a RA, LA, RV and LV BLANK signal on lines 318, 418, 518, and 618 having a duration programmed into RAM/ROM chip 110. The RA, LA, RV and LV BLANK signals are triggered by atrial blanking (AB) and ventricular blanking (VB) trigger signals generated at the outputs of OR gate 314 and OR gate 514, respectively The inputs of OR gate 314 are coupled with the outputs of OR gates 316 and 416 which provide the RA PACE and LA PACE signals delivered to the RA and LA pace output circuits 334 and 434, respectively. The OR gates 316 and 416 pass the RA EI PT and LA EI PT signals selectively generated at the expiration of the V-A escape interval and the RA PT and LA PT generated at the time out of each programmable CDW timed by programmable time delays 330 and 430, respectively.

Similarly, the inputs of OR gate 514 are coupled with the outputs of OR gates 516 and 616 which provide the RV and LV PACE signals delivered to the RV and LV pace output circuits 534 and 634, respectively. The OR gates 516 and 616 pass the RV EI PT and LV EI PT signals selectively generated at the expiration of the AV delay and the RV PT and LV PT signals generated by LV and RV CDW timers 530 and 630 at the time out of each respective programmable CDW.

In this embodiment, an isolated current replicator 325 illustrated in FIGS. 8 and 9 and described further below is interposed between the RA pace/sense electrode pair and the inputs of the RA sense amplifier 326 of the RA pacing channel 300. The RA pace/sense terminals in the connector block 12 are coupled via capacitive filtered feedthroughs through the IPG case to the output current loop of the isolated current replicator 325. The input current loop is coupled with both the input of the RA sense amplifier 326 and the output of the RA pacing output circuit 334. In this embodiment, RA pacing trigger pulses delivered to the input current loop are replicated in the output current loop and delivered to the RA pace/sense electrodes, whereas cardiac signals traversing the RA pace/sense electrodes and the output current loop are replicated in the input current loop and provided to the RA sense amplifier 334.

It will be understood that the RA programmable blanking circuit 336 shown schematically in FIG. 6 can be configured to operate to disconnect the sense amplifier inputs from the input current loop of the isolated current replicator 325 employing blanking switches of the types described above. Therefore, it will be understood that the input current loop of the isolated current replicator 325 can be applied to the inputs of the RA sense amplifier 326 through such blanking switches operated by the RA programmable blanking circuit 336. The RA blanking period provided by the RA BLANK signal is preferably of less than about 100 msec following delivery of an RA pacing pulse or of less than about 7 msec following delivery of any pacing pulse applied to the LA, RV and LV.

Similarly, an isolated current replicator circuit 425 illustrated in FIGS. 8 and 9 described further below is interposed between the LA pace/sense electrode pair and the inputs of the LA sense amplifier 426 of the LA pacing channel 400. The LA pace/sense terminals in the connector block 12 are coupled via capacitive filtered feedthroughs through the IPG case to the output current loop of the isolated current replicator 425. The input current loop is coupled with both the input of the LA sense amplifier 426 and the output of the LA pacing output circuit 434. In this embodiment, LA pacing trigger pulses delivered to the input current loop are replicated in the output current loop and delivered to the LA pace/sense electrodes, whereas cardiac signals traversing the LA pace/sense electrodes and the output current loop are replicated in the input current loop and provided to the LA sense amplifier 434.

It will be understood that the LA programmable blanking circuit 436 shown schematically in FIG. 6 can be configured to operate to disconnect the sense amplifier inputs from the input current loop of the isolated current replicator 425 employing blanking switches of the types described above. Therefore, it will be understood that the input current loop of the isolated current replicator 425 can be applied to the inputs of the LA sense amplifier 426 through such blanking switches operated by the LA programmable blanking circuit 436. The LA blanking period provided by the LA BLANK signal is preferably of less than about 100 msec following delivery of an LA pacing pulse or of less than about 7 msec following delivery of any pacing pulse applied to the RA, RV and LV.

Moreover, an isolated current replicator circuit 625 illustrated in FIGS. 8 and 9 and described further below is interposed between the LV pace/sense electrode pair and the inputs of the LV sense amplifier 626 of the LV pacing channel 600. The LV pace/sense terminals in the connector block 12 are coupled via capacitive filtered feedthroughs through the IPG case to the output current loop of the isolated current replicator 625. The input current loop is coupled with both the input of the LV sense amplifier 626 and the output of the LV pacing output circuit 634. In this embodiment, LV pacing trigger pulses delivered to the input current loop are replicated in the output current loop and delivered to the LV pace/sense electrodes, whereas cardiac signals traversing the LV pace/sense electrodes and the output current loop are replicated in the input current loop and provided to the LV sense amplifier 634.

It will be understood that the LV programmable blanking circuit 636 shown schematically in FIG. 7 can be configured to operate to disconnect the sense amplifier inputs from the input current loop of the isolated current replicator 625 employing blanking switches of the types described above. Therefore, it will be understood that the input current loop of the isolated current replicator 625 can be applied to the inputs of the LV sense amplifier 626 through such blanking switches operated by the LV programmable blanking circuit 636. The LV blanking period provided by the LV BLANK signal is preferably of less than about 100 msec following delivery of an LV pacing pulse or of less than about 7 msec following delivery of any pacing pulse applied to the RA, RV and LA.

In this example, no isolated current replicator is interposed between the RV pace/sense electrode pair and the inputs of the RV sense amplifier 526 and the output of the RV pacing pulse output circuit 534 of the RV pacing channel 500. It will be understood that the locations of the three isolated current replicators 325, 425 and 625 could be changed from the depicted locations or that another isolated current replicator can be interposed between the RV pace/sense electrode pair and the inputs of the RV sense amplifier 526 and the output of the RV pacing pulse output circuit 534. It is also possible to provide switching circuitry that can be enabled by a downlink telemetry command to bypass any of the isolated replicators.

It will be understood that a pair of isolated current replicators could be interposed in each pacing channel to separately isolate the pace/sense electrode pair of the channel from the sense amplifier and the pacing output circuit of each channel.

In operation, assume that the V-A escape interval is being timed out from a preceding ventricular sensed or paced event, and that a spontaneous atrial depolarization occurs in one of the RA or LA and first passes by one of the RA pace/sense electrode pair 17, 19 or the LA CS pace/sense electrode pair 28, 30 (FIG. 5). The SERA signal or the SELA signal is generated when the P-wave is sensed across the pace/sense electrodes 17 and 19 or the LA CS pace/sense electrodes 28 and 30 by the RA sense amplifier 326 or the LA sense amplifier 426, respectively. The first of the SERA or SELA signal to occur during the timing out of the V-A escape interval is employed to reset the current V-A atrial escape interval being timed out in the atrial pacer timing/logic circuit 120A. The first occurring SERA or SELA signal also starts the timing of the respective RA or LA CDW$^S$ time by the respective RA or LA CDW timer 330 or 430. The first occurring SERA or SELA signal is also applied to reset the LA or RA CDW timer 430 or 330, respectively, which would not be timing out any CDW time under this circumstance. An atrial pace pulse is delivered to the other pair of atrial pace/sense electrodes by the RA or LA pacing output circuit 334 or 434 if the RA or LA CDW$^S$ times out without the sensing of the P-wave at the other of the RA or LA CS atrial pace/sense electrodes 17 and 19 or 28 and 30.

Assuming that the V-A escape interval does time out without a P-wave being sensed, then either an RA pace pulse or a LA pace pulse is delivered first by the respective RA pace output circuit 334 or LA pace output circuit 434, respectively, in response to the RA EI PT signal or the LA EI PT signal, respectively. The selection of which atrial pacing pulse is delivered can be programmed. If the RA pace pulse is delivered across the RA pace/sense electrodes 17 and 19, and the LA CDW time is commenced in LA CDW time timer 330. An atrial pace pulse is delivered to the LA CS pace/sense electrodes 28 and 30 if the RA CDW time times out without the sensing of the P-wave at the LA CS pace/sense electrodes 28 and 30.

In either case, the AV delay timer 160 is started to time out an SAV delay on sensing of the P-wave or a PAV delay delivery of the atrial pace pulse. As noted above, preferably separate programmable paced SAV$^{RA}$ and SAV$^{LA}$ delays are employed depending on whether the first atrial sensed event is sensed across the RA pace/sense electrodes 17 and 19 or the LA CS pace/sense electrodes 28 and 30. Separate programmable paced PAV$^{RA}$ and PAV$^{LA}$ delays are also employed depending on whether the first atrial pacing pulsed is delivered across the RA pace/sense electrodes 17 and 19 or the LA CS pace/sense electrodes 28 and 30. These four possible delays are programmed "ON" or "OFF" and the delay values are programmed into RAM/ROM chip 110. The programmed delay values are used in the programmable AV delay timer 160 and started by one of the RSAV, LSAV trigger signals generated by the AV delay select logic or by one of the RPAV and LPAV trigger signals generated by the V-A escape interval timer(s) in atrial pacer timing/logic circuit 120A. Alternatively, only a single RAV or LAV delay can be triggered in response to the RSAV and RPAV trigger signals or the LSAV and LPAV trigger signals, respectively.

In the most general case, if an R-wave is sensed across one pair of the RV or LV CS pace/sense electrodes 38 and 40 or 48 and 50 during the AV time delay, the SERV or the SELV signal is generated by the RV sense amplifier 526 or the LV sense amplifier 626 and applied to reset logic in ventricular pacer timing/logic circuit 120V. A reset signal is generated on line 164 and employed to reset the AV delay timer 160 in FIG. 6. The SERV or the SELV signal is also employed to start a V-A escape interval in ventricular pacer timing/logic circuit 120V, and to start the ventricular CDW time in the respective RV or LV CDW timer 530 or 630. A ventricular pace pulse is delivered to the other pair of ventricular pace/sense electrodes by the respective RV or LV pacing output pulse generator 534 or 634 if the ventricular CDW time times out without the sensing of the R-wave at the other pair of the RV or LV CS pace/sense electrodes 38 and 40 or 48 and 50.

If the V-A escape interval times out, then the ventricular pace pulse is typically first delivered across the RV pace/sense electrodes 38 and 40, and the RV CDW time is commenced in RV CDW timer 530. A ventricular pace pulse is delivered to the LV CS pace/sense electrodes 48 and 50 by the LV pacing output circuit 634 if the ventricular CDW time times out without the sensing of the R-wave at the LV-CS pace/sense electrodes 48 and 50.

Again, in respect to the RA and LA atrial sensing and pacing circuits 300 and 400, the sensing characteristics of the RA and LA sense amplifiers 326 and 426, the CDW times of the CDW time timers 330 and 430 and the pacing pulse output circuits 334 and 434 can be separately programmed and stored in RAM/ROM chip 110. Similarly, in respect to the RV and LV sensing and pacing circuits 500 and 600, the sensing characteristics of the RV and LV sense amplifiers 526 and 626, the CDW times of the CDW timers 530 and 630 and the pacing pulse output circuits 534 and 634 can be separately programmed and stored in RAM/ROM chip 110. Moreover, either or both of the bi-ventricular and bi-atrial operating modes can be optionally programmed off to accommodate particular patients or changes in a particular patient's condition. For example, it may be possible to treat the above-referenced left atrial tachyarrhythmia by programming the above-described bi-atrial pacing mode on and selecting optimum atrial conduction time delays and programming the bi-ventricular pacing and sensing functions off. Conversely, the bi-atrial pacing and sensing functions may be selectively programmed off, and the bi-ventricular pacing and sensing functions optimally programmed to provide the proper therapy for a patient having normal inter-atrial conduction and abnormally long inter-ventricular conduction delays.

It will be understood that the above-described four chamber pacing system of FIGS. 6 and 7 can be selectively configured as two chamber AV sequential pacing system operating in the dual chamber DDD pacing mode, for example, employing at least one current replicator. For example, the left atrial pacing and sensing system 300 and the left ventricular pacing and sensing system 600 and associated components can be eliminated or programmed inoperable providing AV sequential pacing and sensing of the RA and RV wherein the RA isolated current replicator 325 operates in the manner described above. Therefore, it is to be understood that FIGS. 6 and 7 also represent such a dual chamber pacing system that may incorporate the present invention.

Figure 8:
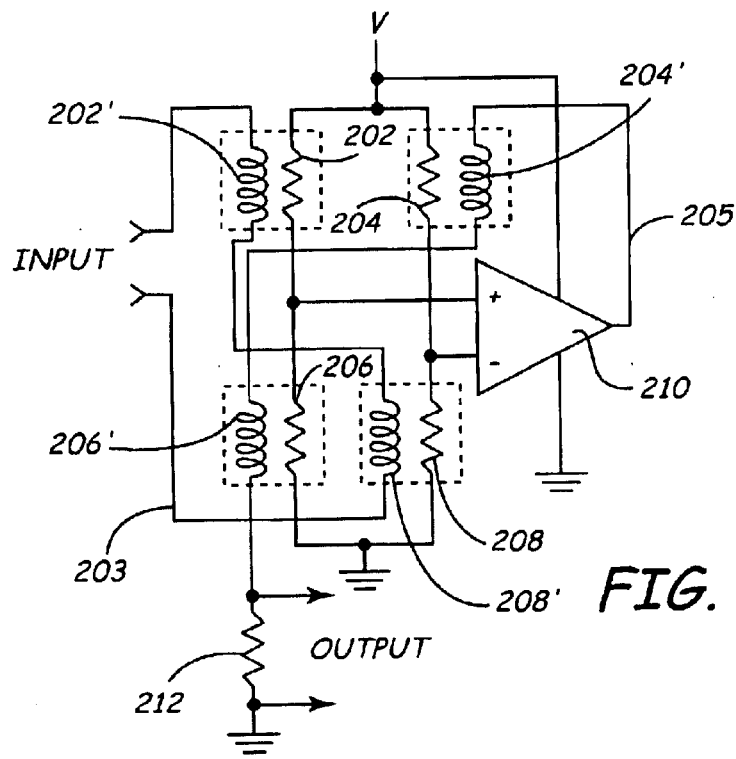
FIG. 8 is a schematic diagram of an illustrative isolated current replicator circuit employing GMR elements in a bridge configuration for isolating up to N−1 sense amplifiers of N sense amplifiers of the circuitry of FIGS. 4 and 6–7 from an associated pair of pace/sense electrodes in accordance with the present invention.
Figure 9:
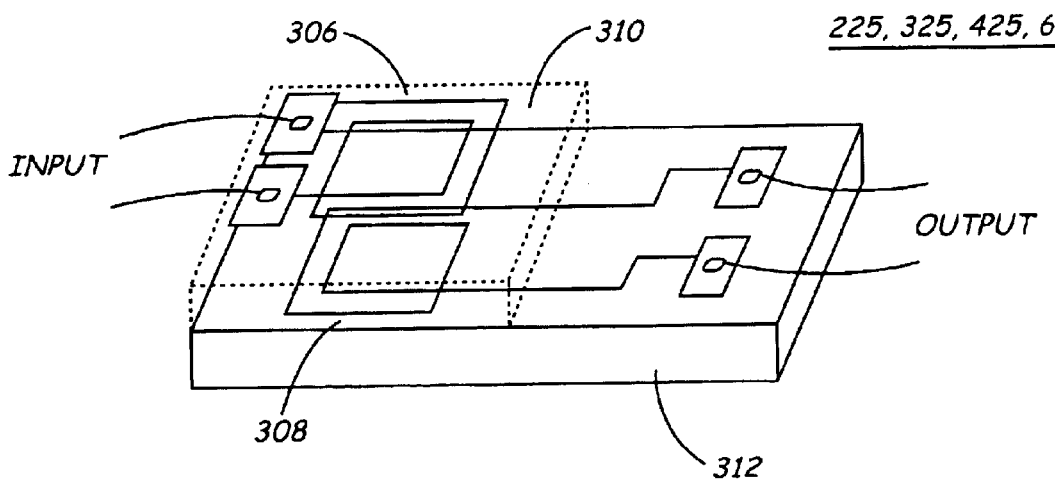
FIG. 9 is a schematic illustration of an isolated current replicator formed employing MEMs fabrication techniques.

Turning to FIG. 8, it schematically illustrates a GMR isolated current replicator usable as the isolated current replicators 225, 325, 425, and 625 of FIGS. 4 and 6–7. The GMR isolated current replicator functions and is preferably fabricated in the manner described in U.S. Pat. No. 6,252, 390 and in the articles by T. M. Hermann et al., entitled "Magnetically Coupled Linear Isolator" (*IEEE Trans. on Magnetics*, vol. 33, no. 5, September 1997, pp. 4029–4031), and by W. L. Hui et al., entitled "Monolithic 4–20 mA Isolating Current Replicator using GMR Resistors" (*ISSC98/Session 17/Sensor Technology/Paper SA* 17.5).

In the recent past, providing magnetic field elements in the form of an intermediate thin layer of a separating material having two major surfaces on each of which an anisotropic ferromagnetic thin-film is formed has been found to lead to a "giant magnetoresistive (GMR) effect" if the thicknesses of the ferromagnetic thin-films and the intermediate layers in such a "sandwich" structure have been made sufficiently small in thickness. This effect can be enhanced by forming such GMR elements with additional alternating ones of these ferromagnetic films and intermediate layers to form superlattices. The resulting enhanced GMR effect can yield a magnetoresistive response in a GMR resistor that can be in the range of up to an order of magnitude greater than that due to the well-known anisotropic magnetoresistive response.

The '390 patent and the Hermann and Hui papers disclose signal isolators, based on magnetoresistive sensing of magnetic conditions occurring therein, that can be advantageously fabricated using ferromagnetic thin-film materials. Such signal isolators can be formed on a surface of a monolithic IC to thereby allow providing convenient electrical connections between an isolator and the operating circuitry therefor.

Each GMR isolated current replicator 225, 325, 425 and 625 depicted in FIG. 8 comprises an input current loop 201 and an output current loop 205 formed as an integrated circuit isolated from one another to block conduction of cross-channel signals. In the preferred embodiments described above, the input current loop 203 is coupled through the blanking switch or switches to the inputs of the sense amplifier and to the output of the pacing pulse circuit of the pacing channel. The output current loop 205 is coupled with the pace/sense electrodes of the pacing/sensing channel across a high value load resistor 212. The input current loop 203 is coupled to the same channel sense amplifier inputs through blanking circuit switches of the same channel blanking circuit. Cardiac depolarization signals can be transferred from the output current loop 205 to the input current loop 203 after the short blanking period of about 5 msec to 10 msec, e.g., 7 msec, following delivery of a cross-channel pacing pulse. The output current loop 205 is isolated from the pacing circuitry coupled to the input current loop 203 due to the GMR elements to prevent cross-channel leakage current accompanying delivery of a pacing pulse in another pacing channel from being applied to the pace/sense electrode pair coupled with the output current loop 205.

In FIG. 8, four magnetically field sensitive GMR resistors 202, 204, 206, and 208 are arranged in a bridge configuration in relation to the input terminals of the conventional IC fabricated operational amplifier (op amp) 210, the regulated supply voltage and ground. The resistors 202, 204, 206, and 208 are formed of GMR material that displays a high magnetic sensitivity and is easily incorporated into a conventional IC processes. The resistance of each GMR resistor 202, 204, 206, and 208 changes as a function of magnetic fields created by a current signal traversing through the respective GMR inductor coil 202', 204', 206' and 208' or each GMR element. Conversely, a current traversing each GMR resistor 202, 204, 206, and 208 induces a current through the respective inductor coil 202', 204', 206' and 208'.

The input current loop 203 is formed of an input current carrying IC conductor formed on an IC substrate having inductor coils 202' and 208' overlying the magnetic field sensitive resistors 202 and 208, respectively. Each GMR resistor 202 and 208 has a first resistance in the absence of magnetic fields created by an input current signal through inductor coils 202' and 208'. When an input current signal is applied to the input current carrying conductor 203 and through coils 202' and 208', respectively, magnetic fields are generated over the respective GMR resistors 202 and 208, causing their resistance to change.

Similarly, output current loop 205 is formed of an output current carrying IC conductor formed on an IC substrate having inductor coils 204' and 206' overlying the magnetic field sensitive resistors 204 and 206, respectively. Each GMR resistor 204 and 206 has a first resistance in the absence of a current signal and a second resistance when a current signal is applied to the output current carrying conductor 205 and induces magnetic fields in coils 204' and 206', respectively. In this case, the current signal in the output current loop 205 can either be generated by the op amp 210 or by an electrical signal traversing the pace/sense electrode pair coupled therewith.

The op amp 210 formed on the IC has a first amplifier input coupled to the first and third giant GMR resistors 202 and 208, a second amplifier input coupled to the second and fourth GMR resistors 204 and 206, and an amplifier output coupled to the output current loop 205. A current in the input current loop 203 is counterbalanced by an isolated, equal feedback current generated by the op amp 210 in the output current loop 205, whereby a pacing pulse can be delivered to the pace/sense electrode pair coupled with the output current loop 205. Conversely, when a cardiac depolarization signal is conducted from the pace/sense electrodes into the output current loop 205, it unbalances the op amp inputs of the op amp 210, causing current to be induced in the input current loop 203 replicating the cardiac depolarization signal.

A pacing pulse generated by the pacing pulse circuit is applied to the input current loop 203 and the signal current causes the first and second GMR resistors 202 and 208 to change in resistance which unbalances the inputs of the op amp 210. The signal generated by the op amp 210 in the output current loop 205 replicates the pacing pulse thereby generating the replicated pacing pulse across resistor 212 and the pace/sense electrode pair.

A cardiac depolarization or other electrical signal traversing the pair of pace/sense electrodes causes a current to be induced in the output current loop 205 and causes the third and fourth GMR resistors 204 and 206 to change in resistance. The change in resistance changes the voltage applied to the inputs of the op amp 210. The current drawn by the op amp 210 to rebalance the inputs causes current to be drawn through the first and third GMR resistors 202 and 208 which induces a current in the respective first and third GMR inductor coils 202' and 208' that is applied through the input current loop 203 to the sense amplifier inputs.

The GMR isolated current replicators 225, 325, 425 and 625 depicted in FIG. 8 can be integrated with standard bipolar and CMOS processes, can substantially reduce hybrid volume, hybrid costs (FAPC) and can provide improved reliability and patient safety over conventional methods for the isolation of the sense amplifiers from the pacing output circuits.

In a further preferred embodiment, monolithic isolation circuits comprising MEMs fabricated isolation transformers are substituted used as the isolated current replicators 225, 325, 425 and 625 of FIGS. 4 and 6–7. Such a monolithic isolation circuit 302 is depicted in FIG. 9, and it comprises MEMs fabricated low-loss input and output coils 306 and 308 separated by an insulation layer 310 that isolates the input coil 306 from output coil 308. This design provides a 2500-volt standoff. Again, this technology could be integrated on top of a standard CMOS wafer 312 allowing similar advantages as described above.

In the above preferred embodiments, it will be understood that the use of the GMR isolated current replicators or MEMS fabricated isolation transformer allows the programming of each $CDW^S$ and $CDW^P$ in a range of from 0 msec to any preferred upper limit. A sensed or paced event in one of the right or left heart chambers triggers substantially simultaneous delivery of a pacing pulse to the other heart chamber when the $CDW^P$ and $CDW^S$ is programmed at 0 msec. The maximum programmable $CDW^S$ and $CDW^P$ is envisaged to be about 100 msec to account for the physiologic activation sequence conduction delays illustrated in FIG. 1. Or a long CDW can be programmed to allow sensing the conducted depolarization and measuring the actual pace triggered or spontaneous conduction delay between any pair of right and left heart chamber pace/sense electrodes. Or the long CDW can be programmed in cases where conduction between right and left heart chambers is absent to provide a highly delayed delivery of a pacing pulse following a sensed or paced event in one heart chamber to the other heart chamber to achieve a particular therapeutic timing of depolarizations of the right and left heart chambers.

However, it will be understood that the above-described pacing systems can be simplified in operation and still enjoy the benefits of use of the GMR isolated current replicators or MEMs fabricated isolation transformers described above. For example, the pacing mode may be programmed to a committed mode that does not time out the CDW rather than the above-described inhibited mode, whereby RHC and LHC pacing pulses are always delivered simultaneously or in a predetermined right-to-left or left-to-right sequence after a pace delay timed from a preceding pacing pulse or sense event. In this case, a simple delay or delay window is timed out from an RHC or LHC pacing pulse or sensed event typically referred to as an A—A delay (atrial) or a V—V delay (ventricular) that is not conditional and results in delivery of an LHC or RHC pacing pulse, respectively, upon time-out. Therefore, "delay window" can refer either to such an A—A delay or V—V delay or the various types of the above described CDWS in RHC-LHC embodiments.

Thus, it can be seen that the present invention can be implemented in any pacing system providing pacing and sensing in at least first and second sites in a single heart chamber or among selected upper and lower, and right and left heart chambers. In bi-atrial or three or four chamber pacing systems, the first site can be one of the right atrium and the left atrium and the second site can be the other the right atrium and the left atrium. In bi-ventricular or three or four chamber pacing systems, the first site can be one of the right ventricle and the left ventricle and the second site can be the other the right ventricle and the left ventricle. In AV sequential pacing systems, the first site can be one of an atrial heart chamber and a ventricular heart chamber and the second site can be the other of the atrial heart chamber and ventricular heart chamber.

Although bipolar atrial and/or ventricular lead systems are depicted in the drawing figures and described above, it will be understood that the present invention may be employed with unipolar lead systems that employ a single pace/sense electrode in the depicted positions in or about the right and left heart chambers and a remote electrode 20 formed as part of the outer surface of the housing of the IPG 12 in FIGS. 2, 3 and 5. Moreover other leads and pace/sense electrodes may be used instead of the depicted leads and pace/sense electrodes that are adapted to be placed at electrode sites on or in the RA, LA, RV and LV.

The preceding specific embodiments are illustrative of the practice of the invention. It is to be understood, therefore, that other expedients known to those of skill in the art or disclosed herein may be employed without departing from the invention or the scope of the appended claims. It is therefore to be understood, that within the scope of the appended claims, the invention may be practiced otherwise than as specifically described without actually departing from the spirit and scope of the present invention.

What is claimed is:

1. A cardiac pacing system comprising:
   a first lead;
   a first sense amplifier having inputs to be coupled to the first lead;
   a first blanking circuit coupled to the first sense amplifier to inhibit sensing of spontaneous cardiac depolarizations during a predetermined blanking interval; and
   a first pace output circuit having outputs to be coupled to the first lead;
   a second lead;
   a second sense amplifier having inputs to be coupled to the second lead;
   a second blanking circuit coupled to the second sense amplifier to inhibit sensing of spontaneous cardiac depolarizations during a predetermined blanking interval; and
   a second pace output circuit having outputs to be coupled to the second lead; and
   pacing timing and control logic coupled to the first and second sense amplifiers, the first and second pace output circuits, and the first and second blanking circuits; and
   a monolithic isolated current replicator coupled between one of the first and second leads and the respective one of the first and second sense amplifiers and comprising an output current loop coupled to the lead and an input current loop coupled to the sense amplifier.

2. The pacing system of claim 1, wherein the pacing timing and control logic comprises:
   an escape interval timer generating a pacing pulse trigger signal upon time-out of an escape interval in the absence of a sensed event signal during the timing of an escape interval; and a delay window timer responsive to the time-out of the escape interval or the sensing of a sensed event signal during the timing of an escape interval to generate a pacing pulse trigger signal upon time-out of a delay window interval.

3. The pacing system of claim 1, wherein the first and second blanking circuits include a switch coupled between the input current loop of the monolithic isolated current replicator and the sense amplifier to uncouple the sense amplifier from the lead during a same channel blanking interval commenced when a pacing pulse is delivered to the same lead that is connected to the sense amplifier and a cross-channel blanking interval is commenced when a pacing pulse is delivered to a different lead than the lead that is connected to the sense amplifier.

4. The pacing system of claim 1, wherein the one of the pace output circuits is coupled to the input current loop of the monolithic isolated current replicator, whereby a pacing pulse generated by the pace output circuit is replicated in the output current loop of the monolithic isolated current replicator and applied to the pace/sense electrodes coupled with the output current loop.

5. The pacing system of claim 4, wherein:

the input current loop of the monolithic isolated current replicator comprises an input current carrying conductor on an integrated circuit substrate and a pair of series-connected inductor coils; and the output current loop of the monolithic isolated current replicator comprises an output current carrying conductor on the integrated circuit substrate and a pair of series-connected inductor coils.

6. The pacing system of claim 5, wherein the monolithic isolated current replicator further comprises a bridge circuit having four magnetically field-sensitive giant magneto-resistive resistors, an operational amplifier having an amplifier input coupled to the bridge circuit and an amplifier output coupled to the output current loop of the monolithic isolated current replicator; and wherein each of the inductor coils in the input current loop of the monolithic isolated current replicator is associated with a respective one of the magnetically field-sensitive giant magneto-resistive resistors in the bridge circuit and each of the inductors in the output current loop of the monolithic isolated current replicator is associated with a respective one of the magnetically field-sensitive giant magneto-resistive resistors in the bridge circuit.

7. The pacing system of claim 4, wherein:

the input current loop of the monolithic isolated current replicator comprises an input current carrying conductor on an integrated circuit substrate and first and second magnetic field inducing coils that generate first and second magnetic fields when a current is present in the input current carrying conductor; and the output current loop of the monolithic isolated current replicator comprises a second current carrying conductor on the integrated circuit substrate and third and fourth magnetic field inducing coils that generate third and fourth magnetic fields when a current is present in the output current carrying conductor; and wherein the monolithic isolated current replicator further comprises:

an operational amplifier formed on the integrated circuit having first and second amplifier inputs and an amplifier output coupled to said output current loop;

a bridge circuit having each of first, second, third and fourth giant magneto-resistive resistors coupled with a respective one of the first, second, third, and fourth magnetic field inducing coils, each giant magneto-resistive resistor having a first resistance in the absence of an applied magnetic field and a second resistance when exposed to a magnetic field generated by a current applied through the magnetic field inducing coil coupled thereto; and a current source coupled to the bridge circuit; and the inputs of the operational amplifier being coupled across the bridge circuit.

8. The pacing system of claim 1, wherein the first lead is adapted for placement in a first heart chamber and the second lead is adapted for placement in a second heart chamber.

9. The pacing system of claim 1, wherein the first lead is one adapted for placement in the right atrium and the second lead is adapted for placement in the left atrium.

10. The pacing system of claim 1, wherein the first lead is adapted for placement in the right ventricle and the second lead is adapted for placement in the left ventricle.

11. The pacing system of claim 1, wherein the first lead is adapted for placement in an atrial heart chamber and the second is adapted for placement in the ventricular heart chamber.

12. The pacing system of claim 1, wherein the monolithic isolated current replicator is formed of a micro-mechanical fabricated (MEMS) isolation transformer comprising low-loss input and output coils separated by an insulation layer that isolates the input coil from the output coil.

* * * * *